(12) United States Patent
Peng et al.

(10) Patent No.: US 6,664,408 B2
(45) Date of Patent: Dec. 16, 2003

(54) PROCESS FOR PREPARING ORGANICALLY-SUBSTITUTED POLYOXOMETALATES

(75) Inventors: Zhonghua Peng, Overland Park, KS (US); Yongge Wei, Beijing (CN); Bubin Xu, Kansas City, MO (US)

(73) Assignee: The Curators of The University of Missouri, Columbia, MO (US)

( * ) Notice: Subject to any disclaimer, the term of this patent is extended or adjusted under 35 U.S.C. 154(b) by 33 days.

(21) Appl. No.: 10/113,962

(22) Filed: Mar. 29, 2002

(65) Prior Publication Data

US 2002/0165405 A1 Nov. 7, 2002

Related U.S. Application Data

(60) Provisional application No. 60/279,967, filed on Mar. 29, 2001.

(51) Int. Cl.$^7$ .............................. C07F 11/00; B01J 31/00; C01G 39/00
(52) U.S. Cl. ........................... 556/57; 556/42; 502/167; 423/594.17; 423/606
(58) Field of Search .................... 556/42, 57; 502/167; 423/606, 594.17

(56) References Cited

U.S. PATENT DOCUMENTS

| | | | | |
|---|---|---|---|---|
| 4,424,164 A | * | 1/1984 | Kroenke ........................ | 556/57 |
| 5,681,973 A | * | 10/1997 | Hoelderich et al. ............ | 556/26 |
| 6,362,355 B1 | * | 3/2002 | Steckel et al. ................. | 556/17 |

OTHER PUBLICATIONS

K. Sonogashira et al. "A Convenient Synthesis of Acetylenes: Catalytic Substitutions of Acetylenic Hydrogen with Bromoalkenes, Iodoarenes, and Bromopyridines" Tetrahedron Letters, No. 50(1975) pp. 4467–4470.

H. Kwen et al. "A Diazoalkane Derivative of a Polyoxometalate: Preparation and Structure of $[MO_6O_{18}(NNC(C_6H_4OCH_3)CH_3)]^{2-}$" Angew. Chem. Int. Ed., vol. 38, No. 8 (1999) pp. 1145–1146.

J. Stark et al., "A Functionalized Polyoxometalate Bearing a Ferrocenylimido Ligand: Preparation and Structure of $[(FcN)Mo_6O_{18}]^{2-}$" Angew. Chem. Int. Ed., vol. 34, No. 22 (1995) pp. 2547–2548.

J. Strong et al. "A New Class of Functionalized Polyoxometalates: Synthetic Structural, Spectroscopic, and Electrochemical Studies of Organoimido Derivatives of $[Mo_6O_{19}]^{2-}$" J. Am. Chem. Soc., vol. 122, No. 1 (2000) pp. 639–649.

Y. Du et al. "A Polyoxometalate Incorporating an Organoimido Ligand: Preparation and Structure of $[Mo_5O_{18(MoNC_6H_4CH_3)}]^{2-}$" J. Am. Chem. Soc., vol. 114, No. 1 (1992) pp. 345–346.

J. Strong et al. "A Superoctahedral Complex Derived from a Polyoxometalate: the Hexakis(arylimido)hexamolybdate Anion $[Mo_6(NAr)_6O_{13}H]$" Chemical Communications, No. 8 (1997) pp. 1137–1138.

A. Teze et al. "About the Keggin Isomers: Crystal Structure of $[N(C_4H_9)_4]_4$-y-$[SiW_{12}O_{40}]$, the y–Isomer of the Keggin Ion, Synthesis and $^{183}W$ NMR Characterization of the Mixed y–$[SiMo_2 W_{10}O_{40}]^{n-}$ (η=4 or 6)" Inorg. Chem., vol. 40, No. 8 (2001) pp. 2000–2004.

W. Clegg et al. "Alkoxide Hydrolysis as a Route to Early Transition–Metal Polyoxometalates: Synthesis and Crystal Structures of Heteronuclear Hexametalate Derivatives" J. Chem. Soc., Dalton Trans., No. 5 (1996) pp. 681–690.

Y. Wei et al. "An Efficient and Convenient Reaction Protocol to Organoimido Derivatives of Polyoxometalates" J. Am. Chem. Soc., vol. 123, No. 17 (2001) pp. 4083–4084.

H. Kang et al. "Co–ordination Complexes of Polyoxomolybdates with a Hexanuclear Core: Synthesis and Structural Characterization of $(NBu^n{}_4)_2[Mo_6O_{18}(NNMePH)]$" J. Chem. Soc., Chem. Commun., No. 13 (1988) pp. 1192–1193.

R. Schroden et al. "Direct Synthesis of Ordered Macroporous Silica Materials Functionalized with Poloxometalate Clusters" Chem. Mater., vol. 13, No. 1 (2001) pp. 1074–1081.

C. Sanchez et al. "Electron Delocalization in Mixed–Valence Molybdenum Polyanions" J. Am. Chem. Soc., vol. 104, No. 9 (1982) pp. 3194–3202.

W. Clegg et al. "Functionalisation of $[Mo_6O_{19}]^{2-}$ with Aromatic Amines: Synthesis and Strucutre of a Hexamolybdate Building Block with Linear Difunctionality" J. Chem. Soc., Chem. Commun., No. 4 (1995) pp. 455–456.

Y. Wei et al. "Functionalization of $[MoW_5O_{19}]^{2-}$ with Aromatic Amines: Synthesis of the First Arylimido Derivatives of Mixed–Metal Polyoxometalates" Inorg. Chem., vol. 40, No. 22 (2001) pp. 5489–5490.

B. Xu et al. "Hybrid Molecular Materials Based on Covalently Linked Inorganic Polyoxometalates and Organic Conjugated Systems" Angew. Chem. Int. Ed., vol. 40, No. 12 (2001) pp. 2290–2292.

C. Mayer et al. "New Hybrid Covalent Networks Based on Polyoxometalates: Part 1. Hybrid Networks Based on Poly-(ethyl methacrylate) Chains Covalently Cross–Linked by Heteropolyanions: Synthesis and Swelling Properties" Chem. Matter., vol. 12, No. 2 (2000) pp. 257–260.

(List continued on next page.)

Primary Examiner—Porfirio Nazario-Gonzalez
(74) Attorney, Agent, or Firm—Senniger, Powers, Leavitt & Roedel

(57) ABSTRACT

The present invention is generally directed to a process for preparing polyoxometalates having amine-derived substituents attached thereto. In a first embodiment, the process comprises contacting a polyoxometalate and an amine in the presence of a diimide. The present invention is further directed to novel functionalized polyoxometalates prepared by the present process.

105 Claims, 1 Drawing Sheet

OTHER PUBLICATIONS

M. Filowitz et al. "$^{17}$O Nuclear Magnetic Resonance Spectroscopy of Polyoxometalates. 1. Sensitivity and Resolution" Inorganic Chemistry, vol. 18, No. 1 (1979) pp. 93–103.

A. Moore et al. "Organoimido–polyoxometalates as Polymer Pendants" Chem. Commun. (2000) pp. 1793–1794.

A. Proust et al. "Phenylimido Derivatives of [$Mo_6O_{19}$]$^{2-}$: synthesis, X–ray strucutres, vibrational, electrochemical, $^{95}$Mo and $^{14}$N NMR Atudies" Inorganica Chemica Acta, vol. 224 (1994) pp. 81–95.

M. Pope et al. "Polyoxometalate Chemistry: An Old Field with New Dimensions in Several Disciplines" Angew. Chem. Int. Ed., vol. 30, No. 1 (1991) pp. 34–48.

J. Stark et al. "Polyoxometalate Clusters as Building Blocks: Preparation and Structure of Bis(hexamolybdate) Complexes Covalently Bridges by Organodiimido Ligands" J. Chem. Soc., Chem. Commun., No. 9 (1995) pp. 1165–1166.

J. Errington et al. "New Aspects of Non–Aqueous Polyoxometalate Chemistry" Kluwer Academic Publishers, M. T. Pope & A. Muller (eds.), Polyometalates: 105–114.

H. Zeng et al. "Poly(polyoxometalate) Dendrimers: Molecular Prototypes of New Catalytic Materials" Angew. Chem. Int. Ed., vol. 39, No. 10 (2000) pp. 1772–1774.

P. Judeinstein "Synthesis and Properties of Polyoxometalates Based Inorganic–Organic Polymers" Chem. Mater., vol. 4, No. 1 (1992) pp. 4–7.

T. Che et al. "Synthesis and Structure of the [($\eta^5$–$C_5H_5$)Ti($Mo_5O_{18}$)]$^{3-}$ and [($\eta^5$–$C_5H_5$)Ti($W_5O_{18}$)]$^{3-}$ Anions" Inorg. Chem., vol. 24, No. 23 (1985) pp. 4055–4062.

E. Coronado et al. "Polyoxometalate–Based Molecular Materials" Chem. Rev., vol. 98, No. 1 (1998) p. 273–296.

P. Gouzerh et al. "Main–Group Element, Organic and Organometallic Derivatives of Polyoxometalates" Chem. Rev., vol. 98, No. 1 (1998) pp. 77–111.

D. Katsoulis et al. "A Survey of Applications of Polyoxometalates" Chem. Rev., vol. 98, No 1 (1998) pp. 359–387.

* cited by examiner

PROCESS FOR PREPARING ORGANICALLY-SUBSTITUTED POLYOXOMETALATES

REFERENCE TO RELATED APPLICATION

This application claims priority from U.S. provisional application, U.S. Serial No. 60/279,967, filed on Mar. 29, 2001, the entirety of which is incorporated herein by reference.

BACKGROUND OF THE INVENTION

The present invention is generally directed to a process for preparing organometallic compounds by means of attaching one or more organic substituents to a central metal-oxygen structure. More specifically, the present invention is directed to a process for substituting or functionalizing polyoxometalates, under mild reaction conditions using readily available reagents, in high yield. The present invention is further directed to novel functionalized polyoxometalates prepared by the present process.

Polyoxometalates ("POMs") are a unique class of metal-oxygen "clusters" or compounds, having multiple metal and oxygen atoms arranged in a cage-like structure, which are generally considered to have extreme versatility in terms of structural, electrochemical and photophysical properties. Additionally, their unique electronic, optical and magnetic properties, as well as high thermal robustness, have made them very attractive in a number of applications, including their potential use (i) as catalysts, (ii) in various medicinal applications, (iii) as sensor or (iv) in other forms of analysis.

The modification of POMs through substitution, such as by the covalent attachment of substituents (e.g., organic species), as a means by which to "fine tune" the various properties of these metal-oxygen clusters, has been the focus of research in the past. For example, many have attempted the direct functionalization of the hexamolybdate anion, $[Mo_6O_{19}]^{2-}$ (the cation typically being a tetrabutylammonium ion). (See, e.g., Y. Du et al., *J. Am. Chem. Soc.*, 1992, 114, 346; W. Clegg et al., *J. Chem. Soc., Chem. Comm.*, 1995, 455; J. B. Strong et al., *Chem. Comm.*, 1997, 1137; J. Stark et al., *Angew. Chem. Int. Ed. Engl.*, 1995, 34(22), 2547; J. Stark et al., *J. Chem., Soc., Chem., Comm.*, 1995, 1165; H. Kwen et al., *Angew. Chem. Int. Ed. Engl.*, 1999, 38(8), 1145; J. B. Strong et al., *J. Am. Chem. Soc.*, 2000, 122, 639; A. Proust et al., *Inorg. Chim. Acta*, 1994, 224, 81; and, W. Clegg et al., *Polyoxometalates: from Platonic Solids to Anti-Retroviral Activity*, (M. T. Pope and A. Muller, eds., Kluwer, Dordrecht, 1994), 113; all of which are incorporated herein by reference in their entireties.) However, to-date, proposed processes have typically employed: (i) the use of phosphinimines (Equation 1, below), which are not readily accessible and which typically yield a mixture of mono- and multi-substituted products, even when the stoichiometry of the reaction is carefully controlled (see, e.g., A. Proust et al. and, W. Clegg et al., *J. Chem. Soc., Chem. Comm.*); (ii) the use of isocyanates (Equation 2, below) which, compared to the phosphinimines, typically enables better control of the reaction product, but which also requires strictly anhydrous reaction conditions, high reaction temperatures and relatively long reaction times (see, e.g., W. Clegg et al., *Polyoxometalates: from Platonic Solids to Anti-Retroviral Activity*; Y. Du et al.; and, J. B. Strong et al.); and, (iii) the use of aromatic amines (Equation 3, below) under high reaction temperatures, which provide only moderate yields, in part due to the great difficulty experienced in isolating the desired product (see, e.g., W. Clegg et al., *J. Chem. Soc., Chem. Comm.*).

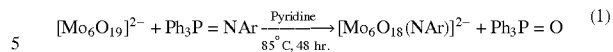  (1)

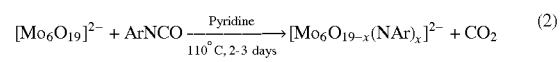  (2)

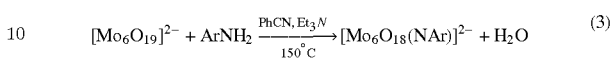  (3)

Accordingly, a need continues to exist for a process which enables the preparation of substituted or functionalized POMs in high yields, by means of a process which is comparatively easy to perform; that is, a need continues to exist for a process whereby POMs may be functionalized under relatively mild reaction conditions and using readily available reagents, thus enabling a wide-range of substituted POMs to be prepared in high yields. In addition, a need continues to exist for such a process which enables a higher productivity to be achieved.

SUMMARY OF THE INVENTION

Among the several features of the present invention, therefore, may be noted the provision of a process for preparing organically substituted or functionalized polyoxometalates, as well as polyoxometalates obtained therefrom; the provision of such a process which enables the economical production of such substituted polyoxometalates; the provision of such a process wherein the substituted polyoxometalates are prepared under mild reaction conditions, including low temperatures and atmospheric pressures; the provision of such a process wherein the substituted polyoxometalates are prepared with a high productivity; the provision of such a process wherein commercially available reagents are employed, enabling a wide-range of substituted polyoxometalates to be prepared; the provision of such a process wherein the substituted polyoxometalates are prepared cleanly and in high yields; the provision of such a process which may be carried out in air and/or in the presence of moisture; and, the provision of such a process which enables functionalized polyoxometalates to be prepared having functionalities that may undergo further reaction or modification in a particular reaction of interest using common synthetic organic chemistry techniques.

Briefly, therefore, the present invention is directed to a process for preparing a polyoxometalate having an amine-derived substituent attached thereto.

The process comprises contacting a polyoxometalate and an amine in the presence of a diimide.

The present invention is further directed to an arylamino-substituted polyoxometalate compound which has an average composition of the formula:

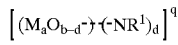

wherein: $(M_aO_{b-d})$ represents the average composition of the metal-oxygen cluster portion of the substituted polyoxometalate, the substituted polyoxometalate comprising one or more metals, M, which may be the same or different, selected from molybdenum, tungsten, vanadium, niobium, tantalum or a combination thereof; and, O is oxygen; N is nitrogen; $R^1$ is a substituent selected from the group consisting of substituted or unsubstituted iodoarylene, alkynylarylene, N-alkylaminoarylene and N,N-dialkylaminoarylene; a represents the number of metal atoms; d represents the number of amine-derived substituents on the polyoxometalate; b–d represents the number of oxygen atoms, the number of oxygen atoms decreasing as the number of amine-derived substituents increases; and, q represents the net charge of the substituted polyoxometalate.

The present invention is still further directed to a process for preparing a bridged polyoxometalate reaction product, wherein two or more metal-oxygen clusters are linked. The process comprises contacting a first reactant polyoxometalate and a second reactant polyoxometalate, each having a substituent which does not comprises a metal-oxygen bond with the reactant polyoxometalate, the substituent on the first reactant polyoxometalate being different from the substituent on the second reactant polyoxometalate, the two reactant polyoxometalates being contacted in the presence of a catalyst capable of catalyzing a coupling reaction between the two different substituents.

The present invention is still further directed to a process for preparing a polyoxometalate having an amine-derived substituent attached thereto. The process comprises contacting a reactant polyoxometalate, a reactant primary or secondary amine, and a reactant activating compound which bonds with a terminal oxygen of the reactant polyoxometalate, forming a leaving group therewith.

The present invention is still further directed to a process for preparing a polyoxometalate having an amine-derived substituent bound thereto. The process comprises contacting a polyoxometalate and an amino-substituted diimide.

Other features of the present invention will be in part apparent and in part pointed out hereinafter.

DETAILED DESCRIPTION OF THE PREFERRED EMBODIMENTS

Figure 1:
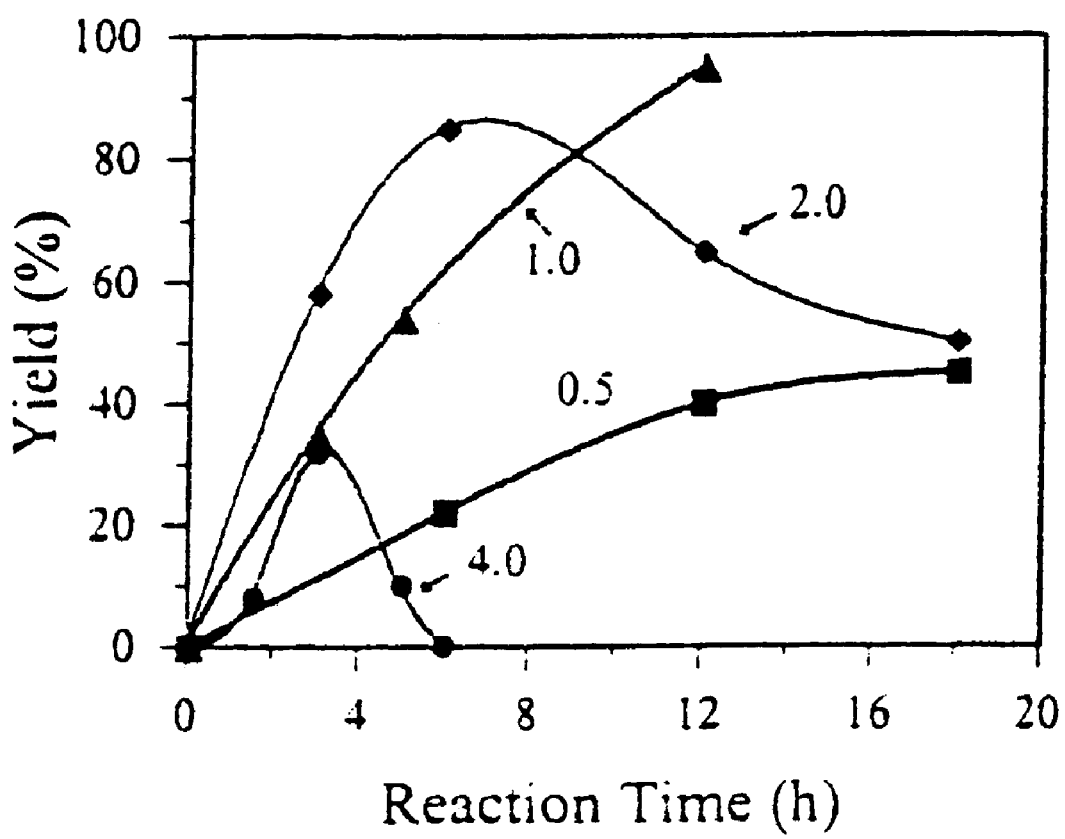
FIG. 1 is a graph which, as further described in Example 1, illustrates the impact different amounts of diimide have on reaction rate and yield of reactions between $[Mo_6O_{19}]^{2-}$ and 2,6-dimethylaniline. (The reactions were carried out in refluxing acetonitrile under a nitrogen atmosphere. The number next to each curve indicates the number of equivalents of dicyclohexylcarbodiimide added to the reacting mixture.)

In accordance with the present invention, it has been discovered that substituted or functionalized polyoxometalates ("POMs") may be prepared in high yields, using mild reaction conditions and relatively short reaction times, which have not heretofore been possible. More specifically, it has been discovered that the use of a diimide reagent dramatically improves or facilitates the reaction of a POM with an amine, and in particular an aromatic amine, or alternatively an amino-substituted diimide. As a result, lower reaction temperatures and shorter reaction times can be employed while still routinely achieving yields of functionalized POMs that have not heretofore been possible. (See, e.g., Y. Wei et al., *An Efficient and Convenient Reaction Protocol to Organoimido Derivatives of Polyoxometalates*, J. Am. Chem. Soc., 2001, 123(17), 4083; and, Y. Wei et al., *Functionalization of $[MoW_5O_{19}]^{2-}$ with Aromatic Amines; Synthesis of the First Arylimido Derivatives of Mixed-metal Polyoxometalates*, Inorg. Chem., 2001, 40(22), 5489; the entirety of which is incorporated herein by reference.)

Because the present process employs an amine to substitute a POM, or alternatively a diimide having an amino-substituent thereon (e.g., R—N=C=N—R—NH$_2$), and further because a vast array of amines are readily available, a wide-range of substituted POMs can advantageously be prepared for further study or use. For example, without being held to a particular theory, it is believed that amine-substituted POMs, sometimes referred to as organoimido POM derivatives, are of particular interest because the organic n-electrons may extend their conjugation through covalent bonding into the inorganic framework of the POM, thus dramatically modifying the redox properties of the metal-oxygen cluster. Additionally, as described herein below, the added functionalities may be used to covalently link POMs or to construct covalently linked POM networks.

Overview—Substituted Polyoxometalates

Generally speaking, the present process enables the preparation of a substituted POM reaction product having the general formula (IA) or (IB):

wherein, as further described herein: N is nitrogen; each of $R^1$ and $R^2$ are independently selected from hydrogen and an organic substituent (e.g., substituted or unsubstituted hydrocarbyl), as further described herein below, or together may form a ring structure; POM is a polyoxometalate to which the amine substituent is bound; d represents the number of amine substituents on the polyoxometalate; and, q represents the net charge of the substituted polyoxometalate (and may be zero or an integer).

In this regard it is to be noted that the bond between the polyoxometalate and the amine substituent, and more specifically between a metal atom of the polyoxometalate and the nitrogen atom of the amine substituent, is represented by a dashed line because the nature of the bond may vary with the type of amine (e.g., primary or secondary) that is reacted with, and ultimately bound to, the POM. For example, as further described herein below, it is generally believed that a primary amine forms a bond which is "triple bond-like" in character with the POM.

Synthesis of Substituted Polyoxometalates

In a first embodiment, the process of the present invention generally comprises contacting: (i) a correspondingly unsubstituted polyoxometalate (i.e., a POM having substantially the same composition or configuration as the substituted POM but without the amine substituent attached thereto, instead having an oxygen atom at this location on the metal-oxygen cluster, as further described herein); (ii) a corresponding amine (i.e., an amine having substantially the same composition or configuration as the amine substituent(s) attached to the POM, but with one or more hydrogen atoms bound thereto in place of one or more bonds to the POM); (iii) a diimide; and, optionally, (iv) a suitable solvent in a reaction zone by means common in the art and as further described herein.

The amine, from which the amine substituent is derived, has the general formula (II):

$$NHR^1R^2 \qquad (II)$$

wherein: N, $R^1$ and $R^2$ are as previously defined, and H is hydrogen. The substituents, $R^1$ and $R^2$, may be the same or different and are typically hydrogen or substituted or unsubstituted hydrocarbyl. More specifically, in one embodiment, $R^1$ and $R^2$ are selected from hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted allyl, substituted or unsubstituted aryl, substituted or unsubstituted heteroaryl, or a combination thereof. In some preferred embodiments, $R^1$ and/or $R^2$ are selected from alkyl groups having from about 1 to 20 carbon atoms (e.g., methyl, ethyl, propyl, butyl, pentyl, hexyl, etc.) or aryl groups (e.g., phenyl, benzyl, naphthyl, etc.), including such groups which are also substituted, having, for example, halo (e.g., chloro, iodo, bromo, fluoro, etc.), hetero (e.g., nitrogen, oxygen, etc.), alkenyl (e.g., ethenyl, propenyl, butenyl, etc.) or alkynyl (e.g., ethynyl, propynyl, butynyl, etc.) substituents attached thereto. In some particularly preferred embodiments, primary amines are reacted with the polyoxometalate of interest; that is, in some particularly preferred embodiments, one of $R^1$ and $R^2$ is hydrogen. Among the preferred primary amines are haloarylamines (e.g., iodophenylamine, bromophenylamine, etc.), alkenylarylamines (e.g., ethenylphenylamine, propenylphenylamine, etc.) and alkynylarylamines (e.g., ethynylphenylamine, propynylphenylamine, etc.).

In this regard it is to be noted that $R^1$ and $R^2$ may be other than herein described without departing from the scope of the present invention. Generally speaking, $R^1$, $R^2$ or a combination thereof may be essentially any substituent, provided they do not reduce the nucleophilicity of the nitrogen of the amine reactant, such that it will not react and bond with the polyoxometalate of interest.

Polyoxometalates, including heteropolyoxometalates (wherein different metal atoms are present in the same metal-oxygen cluster) are well known in the art, and are commercially available or can be prepared in various forms by means known in the art. (See generally, for example: M. T. Pope et al., *Heteropoly and Isopoly Oxometalates* (Springer-Verlag, New York 1983); M. T. Pope et al., *Chemistry of Polyoxometallates. Actual Variations on an Old Theme with Interdisciplinary References*, Ange. Chem., Int'l. Ed. Engl., 1991, 30, 34; *Polyoxometalates: From Plantonic Solids to Anti-Retroviral Activity*; M. T. Pope and A. Muller, eds. (Kluwer Academic Publishers, The Netherlands 1994); C. L. Hill, Chem. Rev., 1998, 98, 8; and, Y. Ishii et al., J. Mol. Cat., 110, 105 (1996); the entirety of which is incorporated herein by reference.) In general, a POM has a cage-like framework, such as that illustrated in (III), below, which comprises a plurality of metal atoms, and optionally certain non-metals, bound to oxygen atoms.

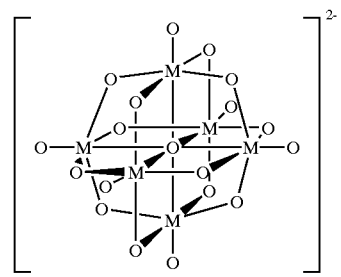

(III)

However, it is to be noted that polyoxometalates are known to exist in a variety of different structures, the different structures corresponding to specific geometries of particular compositions and varying according to the coordination chemistry and atomic radii of the atoms present. This structure should therefore not be viewed in a limiting sense.

Accordingly, the polyoxometalates of the present invention may more generally be represented by the formula (IV):

$$(M_aO_b)^t \qquad (IV)$$

wherein: M represents metal atoms, and optionally certain non-metal atoms other than oxygen; O represents oxygen atoms bound to the metal atoms of this metal-oxygen cluster; subscript a represents the number of metal and non-metal atoms (other than oxygen); subscript b represents the number of oxygen atoms (the number of oxygen atoms being at least in part dependent upon the number of metal and other non-metal atoms present and sufficient to satisfy the valences of the metal and other non-metal atoms, except for the charge, t); and, superscript t represents the charge of the POM. It is to be noted that, because the metal and/or the non-metal atoms may be the same or different, in some instances the POM may alternatively be represented by, for example, formulas (V) and (VI):

$$(M^1_pM^2_yO_b)^t \qquad (V)$$

$$(M^1_pM^2_yM^3_zO_b)^t \qquad (VI)$$

wherein $M^1$, $M^2$ and $M^3$ represent different metal or non-metal atoms of the POM, and p+y or p+y+z represent the total number of metal and non-metal atoms (other than oxygen) present in the POM.

In this regard it is to be noted that the above-referenced formulas (e.g., IA, IB, III, IV, V, VI) generally represent the average composition of the polyoxometalates, as further described herein below.

In one embodiment of the present invention, the polyoxometalate typically comprises a metal, M, selected from molybdenum, tungsten, vanadium, niobium and tantalum, as well as combinations thereof, with molybdenum, tungsten, or a combination thereof being preferred. However, it is to be noted that, in other embodiments, the POM may alternatively or additionally comprise (i) a non-metal such as phosphorus, boron, silicon, antimony, arsenic, (ii) a metal such as germanium and gallium, or (iii) a metal such as iron, zinc or titanium, as well as combinations thereof.

The number of metal atoms, or metal and non-metal atoms, varies with the size of the metal-oxygen cluster or cage, in some instances ranging from a few atoms (e.g., about 2, 3, 4, 6 or more) or tens of atoms (e.g., about 10, 25, 50, 75 or more), up to a few hundred atoms (e.g., about 100, 150, 200, 250 or more). In one embodiment, however, the POM typically comprises about 2 to about 10, or about 4 to about 8, metal atoms, with about 6 being preferred.

Similarly, while the number of oxygen atoms in the cluster or cage will also vary with its size (and the number of metal atoms, the number of oxygen atoms increasing at the number of metal atoms increases), in some instances subscript b (of formula IV, above) ranges from a few atoms (e.g., about 2, 4, 6, 8 or more) to several tens of atoms (e.g., about 10, 25, 50, 75 or more), up to a few hundred atoms (e.g., about 100, 125 or more). In one embodiment, however, subscript b typically ranges from about 10 to about 30, or from about 15 to about 25, with about 19 being preferred.

Common POMs include, for example, those having the average composition of formula $M_6O_{19}$, $M_7O_{23}$, $M_{12}O_{40}$ (sometimes referred to as the Keggin form) or $M_{18}O_{62}$ (sometimes referred to as the Dawson form). Furthermore, in some embodiments of the present invention, preferred POMs include those having the average composition of formula $M_6O_{19}$, wherein M is molybdenum only, or molybdenum and one or more of tungsten, vanadium or silicon (the number of molybdenum atoms in the average composition preferably being 1, 2, 3 or more).

It is to be noted that, as used herein, "polyoxometalate" is intended to refer to the present metal-oxide or metal-oxygen clusters or cages in all their various forms, including the acid (i.e., wherein all cations associated with the polyoxometalate anion, as described herein, are protons), the salt (i.e., wherein the cations are not hydrogen, but rather are, for example: ammonium ions; alkylammonium ions, such as tetramethylammonium, tetraethylammonium, tetrabutyammonium, etc.; alkali metals, such as sodium ions, potassium ions, etc.; or combinations thereof), or the acid salt forms (wherein a combination of protons and others cations are present). Accordingly, in some embodiments the POM may have no charge, or a negative charge typically ranging from about −2 to about −50, −25 or −10, with a charge ranging from about −2 to about −6 being most common in at least some embodiments.

The number of substituents, d, attached to the polyoxometalate is at least in part dependent upon the size of the metal-oxygen cluster. Typically, however, the number of substituents is less than about 25, 20 or even 15, with d ranging from about 1 to about 12, 2 to about 8 or 3 to about 6 in some embodiments. In some preferred embodiments, such as when the POM has an average composition of formula $M_6O_{19}$, d ranges from about 1 to about 6, or from about 2 to about 4. In this regard it is to be noted, however, that in some embodiments the number of substituents is at least in part dependent upon the number of molybdenum atoms present in the POM. Without being held to any particular theory, it is generally believed that, when molybdenum is present, reaction occurs preferentially, and in some instances exclusively, at these sites.

It is to be noted that, in a second or alternative embodiment, the substituted polyoxometalate of the present invention is generally prepared by contacting a polyoxometalate and an amino-substituted diimide, and optionally a suitable solvent, in a reaction zone by means known in the art and as further illustrated herein below.

Reaction Conditions

Referring now to Equation (4), the general reaction scheme for one embodiment of the present invention is presented (wherein a primary amine, $R^2$ therefore being hydrogen, and a diimide are reacted with a polyoxometalate):

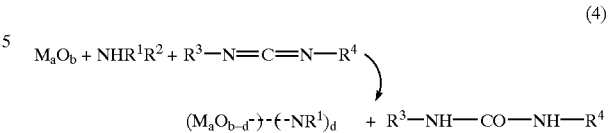

(4)

wherein $R^3$ and $R^4$ may be the same or different and are typically substituted or unsubstituted hydrocarbyl. In one embodiment, $R^3$ and $R^4$ are independently selected from substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted allyl, substituted or unsubstituted aryl, substituted or unsubstituted heteroaryl, or a combination thereof. In some preferred embodiments, $R^3$ and $R^4$ are independently selected from alkyl groups having from about 1 to 20 carbon atoms (e.g., methyl, ethyl, propyl, butyl, pentyl, hexyl, etc.) or cycloalkyl groups (e.g., cyclopentyl, cyclohexyl, etc.), including such groups which are also substituted.

In this regard, it is to be noted that, as describe herein, in some alternative embodiments, (i) the amine may be secondary (i.e., $R^2$ is other than hydrogen), yielding a polyoxometalate having a substituent $NR^1R^2$; and/or, (ii) the amine may be part of the diimide itself (e.g., the POM reacts with a diimide $R^3$—N=C=N—$R^4$—$NH_2$, wherein in this case the diimide is, for example, the $R^1$ substituent of the amine and $R^2$ is hydrogen), the resulting reaction product being a substituted polyoxometalate having a urea-like substituent (i.e., the urea reaction product referenced in Equation 4, above, being part of the POM substituent in this instance).

In general, the process of the present invention may be carried out using means common in the art. While the reaction may be conducted at high temperatures and/or above atmospheric pressures, the present invention is advantageous in that mild reaction conditions may be employed. More specifically, the present reaction may be carried out atmospheric pressure and at a temperature ranging from greater than about room temperature (e.g., about 25° C.) to less than about 150° C., from about 50° C. to about 125° C., or from about 75° C. to about 100° C. However, in one embodiment, the temperature typically is greater than about 25° C. and less than about 80° C., 70° C. or even 60° C. Alternatively, however, the reaction can be carried out at the reflux temperature of the reacting mixture.

In the process, essentially any suitable solvent may be employed. In one embodiment, for example, a polar aprotic solvent is used, such as acetonitrile, pyridine, benzonitrile, N,N-dimethylformamide, as well as other amide-type solvents. However, one advantage of the present invention is that relatively inexpensive solvents, such as acetonitrile, can be employed. Alternatively, however, it is to be noted that, when the amine employed is a liquid, the reaction may be run neat; that is, when the amine is a liquid, a solvent may be optional (the amine, in this case, effectively acting as a reagent and solvent). Such an approach may be utilized, for example, when multiple substitutions on the polyoxometalate are desired, as the amine will be in excess relative to the polyoxometalate (the excess amine, and diimide (the ratio being for example about 1:1), typically resulting in multiple substitutions of the polyoxometalate).

Among the other advantageous features of the present invention is that the process need not be carried out under anhydrous conditions or under an inert atmosphere (e.g., nitrogen, argon, etc.). Stated another way, while in at least one embodiment the present process is preferably carried out in the absence of water and under an inert atmosphere, the process may alternatively be performed in air and in the presence of moisture (e.g., water and/or water-vapor). In the latter case, however, additional diimide may be desirable in order, for example, to consume or react with the excess moisture present.

Additionally, the present process enables yields of about at least about 50%, 60%, 80%, 90%, 95% or more (based on the initial, molar amount of reactant POM) of the functionalized POM product to be obtained, with reaction times of less than about 48 hours, 24 hours, or even 12 hours (e.g., about 10 hours, 8 hours or less), with a reaction time ranging from about 1 to 48 hours, about 4 to 24 hours, or about 8 hours to 12 hours being preferred in some embodiments (such as those wherein about 1 to 1.2 equivalents of diimide per equivalent of POM and amine is used).

In this regard it is to be noted that experience to-date suggests that, in at least some embodiments, allowing the reaction to run too long, such as beyond the point of amine exhaustion, may actually have a detrimental impact on yield (see, e.g., Example 1, below). Accordingly, it at least some embodiments shorter reaction times (e.g., less than about 12, 10, 8, 4 or even 2 hours) is preferred. Without being held to a particular theory, this decrease in yield is believed to be the results of reaction product decomposition to the parent metal-oxygen cluster (e.g., $M_6O_{19}$) under the reaction conditions employed (e.g., exhaustion of reactant amine, coupled with excess diimide which facilitates decomposition of the reaction product).

It is to be further noted, again without being held to a particular theory, that, as illustrated in the reaction mechanism presented below, it is believed the diimide reactant in the present process "activates" a terminal metal-oxygen bond of the POM (i.e., a metal-oxygen bond wherein the oxygen atom is bound to a single metal atom, such as molybdenum), incorporating the oxygen atom into an enhanced leaving group, while at the same time increasing the electrophilicity of the metal atom to which it is bound. As a result, the oxygen atom is replaced by the nitrogen atom of the amine, resulting in the attachment of the amine substituent on the metal-oxygen cluster.

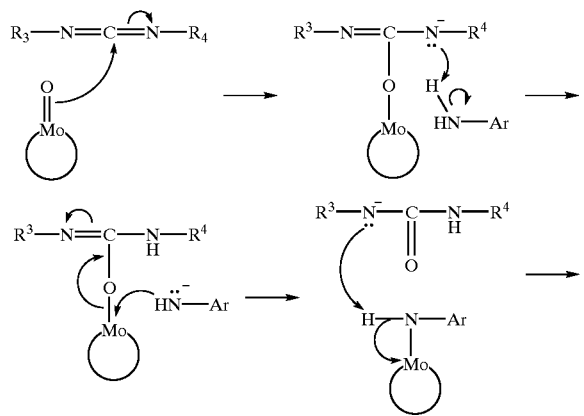

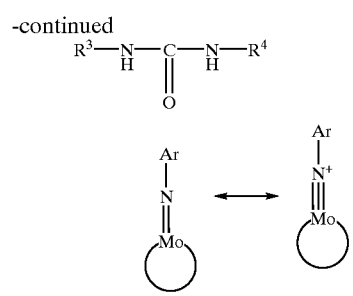

Additionally, as the above reaction mechanism illustrates, the diimide also acts as a base, abstracting one or more protons from the amine nitrogen (before, and potentially after, attachment to the polyoxometalate). Accordingly, although essentially any reagent capable of activating the metal-oxygen bond, forming a leaving group with the oxygen thereof, and abstracting one or more protons from the amine nitrogen in this way may be used in the present invention, in one preferred embodiment a diimide, and preferably a carbodiimide (such as diethylcarbodiimide, diisopropylcarbodiimide or, more preferably, dicyclohexylcarbodiimide or "DCC"), is used.

With respect to the nature of the bond between the POM, or more specifically a metal atom of the POM, and the nitrogen atom of the amine substituent, as previously noted, this may vary with the type of amine used on the reaction. For example, without being held to a particular theory, it is generally believed that the nitrogen atom of a primary amine forms a bond with the metal which is "triple bond-like" in character. As a result, while secondary, and possibly even tertiary, amines (including for example heterocycles) may potentially be employed to form a substituted or functionalized POM in some embodiments, primary amines are generally preferred because a more stable product is formed. Accordingly, in one preferred embodiment, a primary amine is used.

In this regard it is to be further noted that the metal-nitrogen bond is described as "triple bond-like" because the bonding configuration at this location (i.e., the metal-nitrogen-carbon bond angle) is about 180°, as determined by X-ray crystallographic studies. (See, e.g., Y. Wei et al., J. Am. Chem. Soc., 2001, 123(17), 4083; and, Y. Wei et al., Inorg. Chem., 2001, 40(22), 5489; the entirety of which is incorporated herein by reference.)

Generally speaking, reagent stoichiometry will typically be controlled to achieve the desired product in the highest possible yield for the given reaction conditions. In one embodiment, however, the molar ratio of diimide (or analogous reagent) to reactant POM ranges from about 20:1, 15:1, 10:1, 5:1 or even 2:1 to about 1:2, or from about 1.5:1 to about 1:1.5, with about 1.5:1, 1.2:1 or 1:1 being preferred in some embodiments (high ratios typically being used when multiple substitutions of the POM are to be achieved). Similarly, the molar ratio of amine to reactant POM typically, and in some instances independently of the ratio of diimide to POM, ranges from about 20:1, 15:1, 10:1, 5:1 or even 2:1 to about 1:2, from about 1.5:1 to about 1:1.5, with about 1:1.5, 1:1.2 or 1:1 being preferred (high ratios typically being used when multiple substitutions of the POM are to be achieved).

Additionally, again generally speaking, in at least some embodiments the molar ratio of diimide to amine may range from about 2:1 to about 1:2. However, it is to be noted that preferably the ratio of amine to POM increase as the ratio of diimide to POM increases, or vice versa; that is, preferably a large excess of diimide to amine is typically not used, as this may detrimentally impact yield of the reaction product (excess diimide reaction with the reaction product, leading to the decomposition thereof). Accordingly, in a preferred embodiment, the ratio of diimide to amine ranges from about 1.5:1 to about 1:1.5, with about 1.5:1, 1.2:1 or 1:1 being preferred. In some particularly preferred embodiments, the molar ratio of diimide to amine to POM is about 1:1:1, or alternatively about 1.5:1:1.

In this regard it is to be noted that experience to-date suggests the amount of diimide to be used or added to the reacting mixture is in at least some instances generally related to the amount of amine added, which in turn impacts the number of substituents on the substituted POM product (i.e., the degree of substitution). For example, if a ratio of diimide to amine to POM of 1:1:1 is used, a substantially single substituted POM will result. However, as the ratio of diimide and amine to POM increases, a mixture of single, di-, tri- etc. substituted POM may result, while a ratio of 2:2:1 typically results in a primarily bifunctionalized POM reaction product.

It is to be further noted that experience to-date suggests, in at least some instances, as the number of equivalents of diimide increases, the rate at which reaction product is formed increases. However, a large excess of the diimide (e.g., 2, 3, 4 or more equivalents) may detrimentally impact yield of the reaction product (i.e., the substituted POM). Without being held to a particular theory, it is generally believed that this is due a reaction between excess diimide and the initially formed reaction product.

It is to be still further noted experience to-date suggests that, in some instances, the POM may be an oxidant strong enough to oxidize the reactant amine, rather than form a bond (e.g., an imine bond) with it, such as when the POM is a Keggin ion (having an average composition of formula $M_{12}O_{40}$). It may therefore be necessary to reduce the POM, using means known in the art (by exposing it to a reducing agent, such as Zn powder, hydrazine (i.e., $NH_2NH_2$), $SnCl_2$, etc., or by using an electrochemical method, such as by controlling the cathode voltage), before a substitution reaction with the amine is performed. The resulting substituted POM can later be oxidized to the desired state or form, again using means known in the art. However, in an alternative approach, an aromatic amine (or some other amine less susceptible to oxidation by the POM) may be used.

Substituted Polyoxometalates

As previously stated, the present process enables the preparation of substituted or functionalized polyoxometalates in high yields using mild reaction conditions. Since this process allows for the use of readily available reagents, a wide-range of products can be prepared, including functionalized POMs which have not heretofore been prepared. For example, in accordance with the present invention, alkenylarylamino-substituted, alkynylarylamino-substituted, and haloarylamino-substituted POMs, as well as alkoxyarylamino-substituted and heteroarylamino-substituted POMS, such as those capable of forming the anions presented below (1–10, as well as 11–13), may be prepared using, for example, the following reaction scheme (Equation 5):

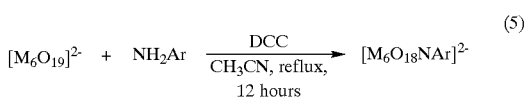

(5)

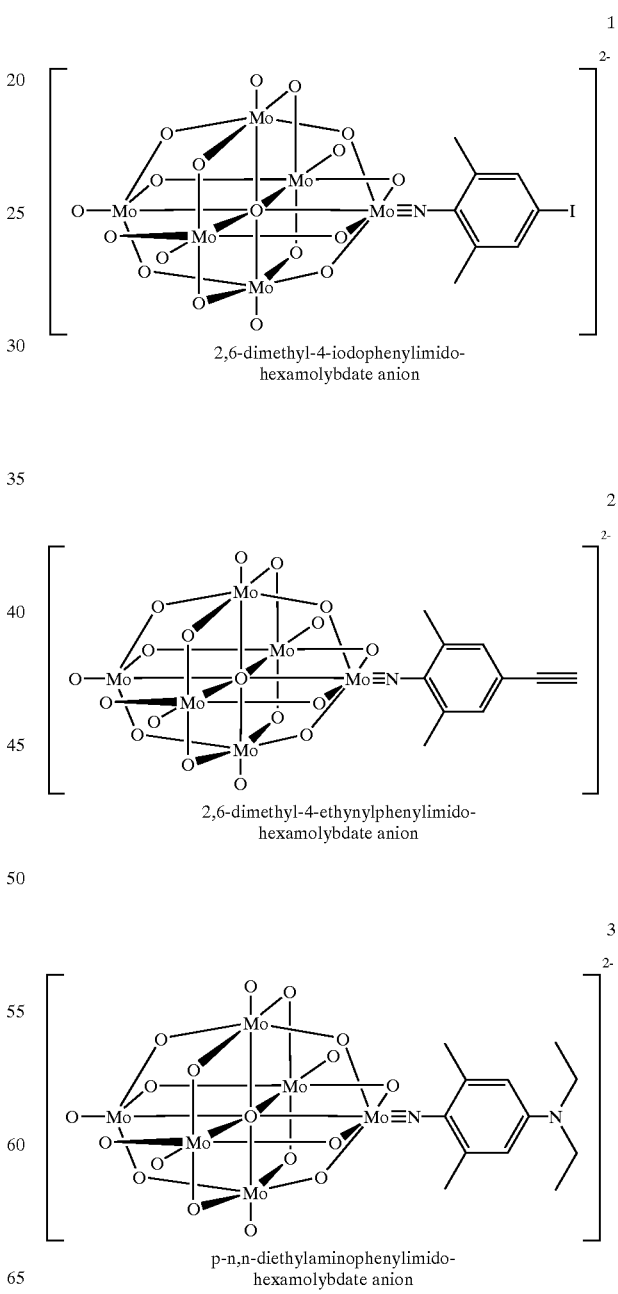

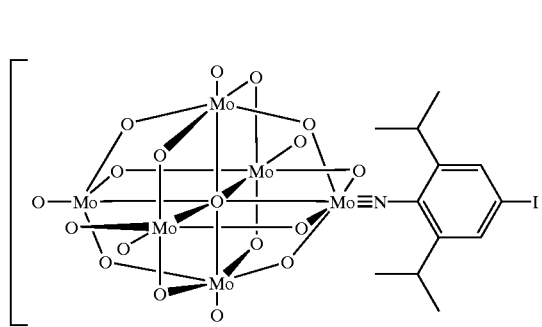

4

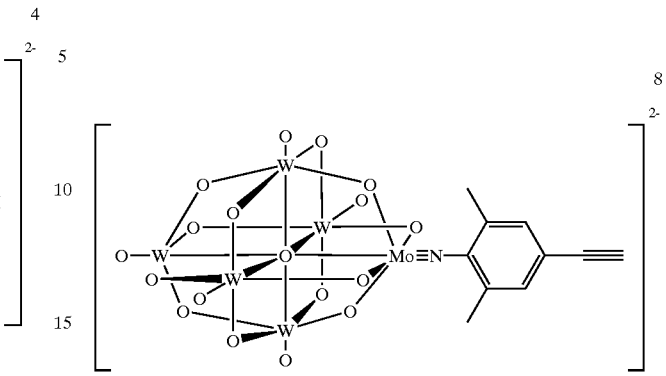

8

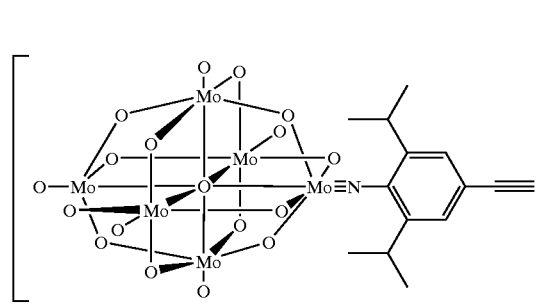

5

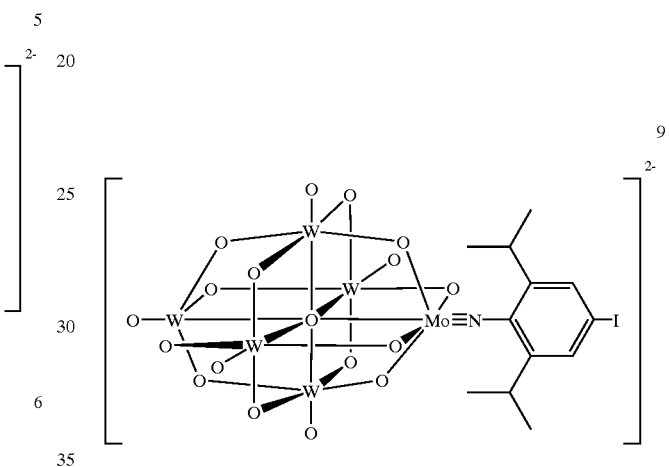

9

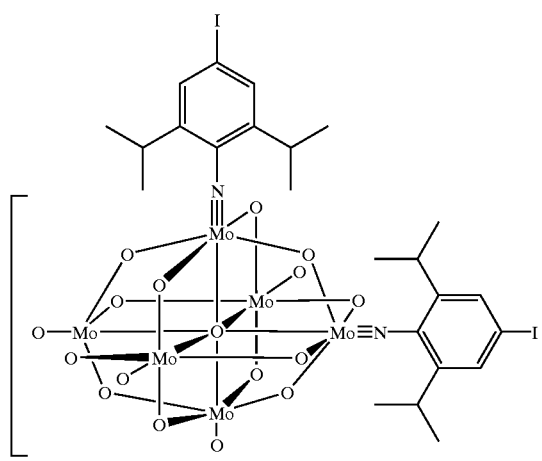

6

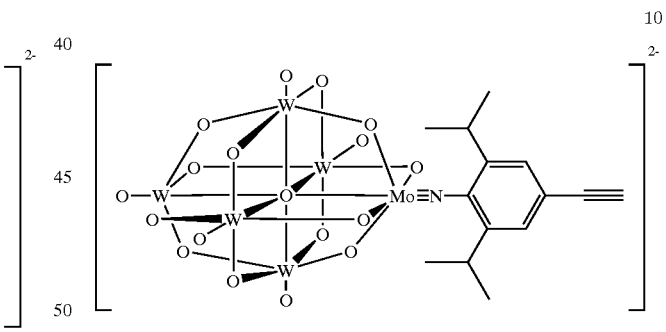

10

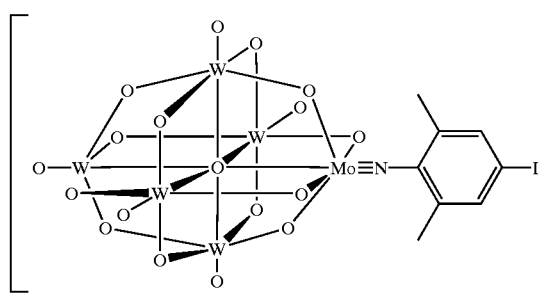

7

It is to be noted that the present invention additionally enables the preparation of substituted POMs having sites or functional groups, such as those presented above or described elsewhere herein (e.g., POMs having halo and alkenyl or alkynyl substituents), that may then undergo further reaction using means common in the art, such as a catalyzed coupling reaction (e.g., palladium catalyzed coupling), as generally illustrated in the reaction scheme presented below (Equation 6), to yield additional novel, substituted POMs, including those capable of forming the anions presented below (e.g., 11–16):

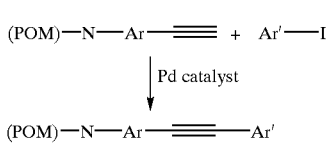
(6)
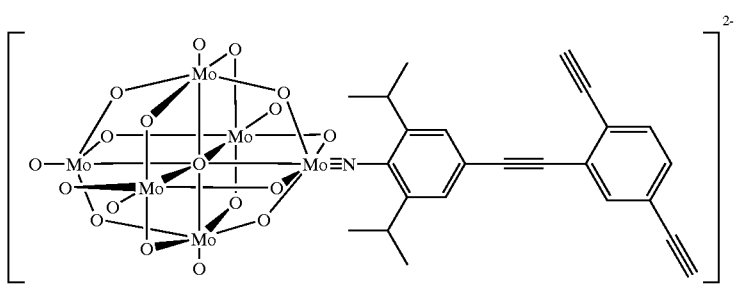
11
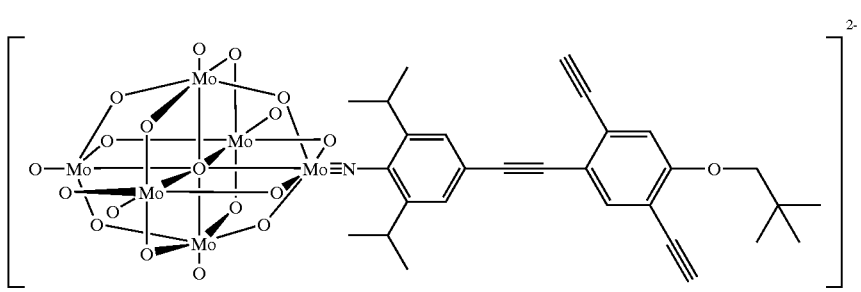
12
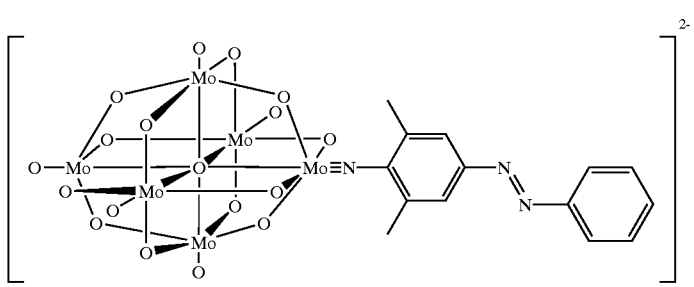
13
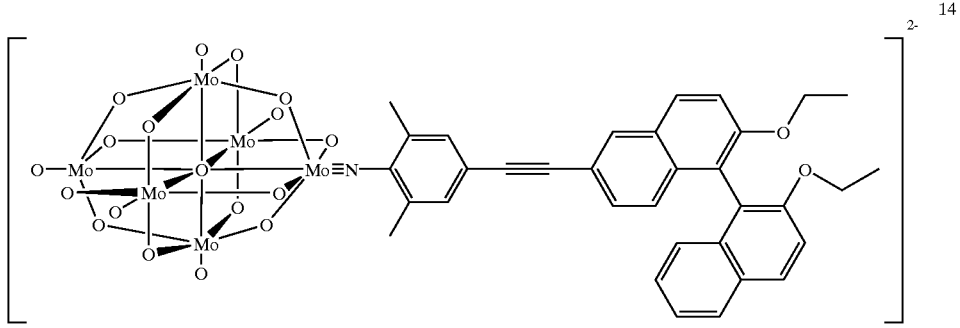
14
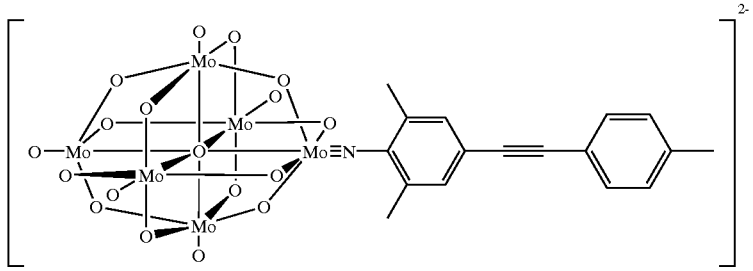
15

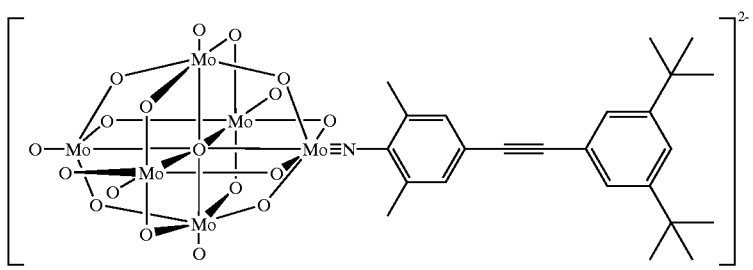

(See, e.g., B. Xu et al., *Hybrid Molecular Materials Based on Covalently Bonded Inorganic Polyoxometalates and Organic Conjugated Systems*, Angew. Chem., 2001, 113 (12), 2353, Angew. Che. Int'l. Ed., 2001, 40(12), 2290; the entirety of which is incorporated herein by reference.) Catalyst suitable for such reactions are known in the art and include, for example, palladium catalysts (e.g., Pd(OAc)$_2$, Pd(PPh$_3$)$_2$Cl$_2$, Pd(PPh$_3$)$_4$, Pd$_2$(dba)$_3$ (wherein "dba" is trans,trans-dibenzylideneacetone), Pd(dppf)Cl$_2$ (wherein "dppf" is 1,1'-bis-(diphenylphsphanyl0ferrocene)), nickel catalysts (e.g., NiCl$_2$L$_2$, wherein L is a phosphine ligand, such as PPh$_3$, etc.), and copper/lithium catalysts (e.g., R$_2$CuLi). In at least some embodiments, however, palladium catalysts are preferred.

In addition, two functionalized or substituted POMs, such as those prepared in accordance with the present invention, may be coupled or linked in a similar manner, as illustrated for example in Equation 7 below:

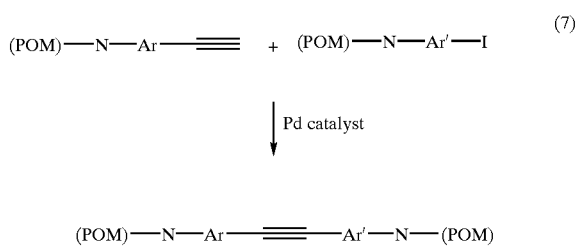

Such an approach may be utilized to prepare coupled or "dumbbell" POMs, wherein two metal-oxygen clusters are bridged by a reaction between different amine substituents attached thereto. (See, e.g., M. Lu et al., *Hybrid Molecular Dumbbells: Bridging Polyoxometalate Clusters with an Organic π-Conjugated Rod*, Angew. Chem. Int'l. Ed. (accepted for publication); and, Y. Wei et al., Inorg. Chem., 2001, 40(22), 5489; the entirety of which is incorporated herein by reference.) Exemplary compounds are presented below:

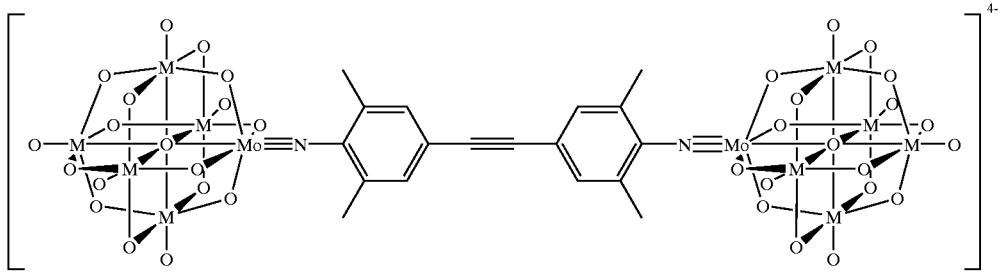

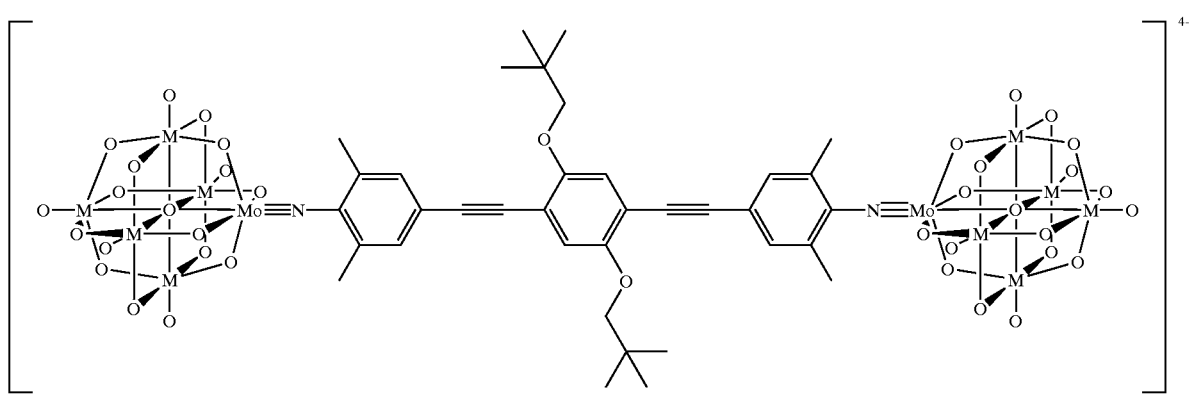

wherein M is, for example, molybdenum or tungsten. Such are of particular interest because of the potential for the organic π-electrons to extend their conjugation to the inorganic framework through the extended, π-conjugated organic "bridge."

It is to be noted that, for the above-referenced compounds, one or more of the molybdenum and/or tungsten atoms in the illustrated compounds could be replaced with a different metal or non-metal referenced herein to yield additional novel compounds. Accordingly, the above structures are intended to illustrate the types of novel compounds than can be prepared by the present invention and, therefore, should not be viewed in a limiting sense.

It is to be further noted that other functional groups may be used for the coupling or linking reaction; for example, in addition to functional groups having unsaturated bonds, haloarylamine-substituted POMs or compounds may react or couple with compounds or POMs having functional groups derived from boronic acids (e.g., —B(OH)$_2$), boronic acid esters (e.g., —B(OR)$_2$), trialkylstannyls (e.g., —SnR$_3$), and triflates (i.e., trifluoromethanesulfonyls, —OTf), by means known in the art (including by means employing the catalysts described herein above). In addition, it is to be noted that other functional groups could similarly be attached and subsequently reacted with other compounds or POMs, the selection of such functional groups and the reaction conditions to be used therewith being known to those skilled in the art. Accordingly, the above structures, functional groups and reaction conditions are intended to be illustrative and, therefore, should not be viewed in a limiting sense.

In view of the foregoing it is to be noted that, in comparison to processes currently known in the art, the present invention enables the production of functionalized or substituted polyoxometalates in higher yields (e.g., 90%, 95% or more) with milder and less stringent process conditions (e.g., reaction temperatures of about 80° C., 70° C., 60° C. or even 50° C., optionally performed in air and/or a non-anhydrous environment or atmosphere) and relatively short reaction times (e.g., less than about 12 hours, 10 hours or even 8 hours).

Definitions:

As used herein, in some embodiments the terms below typically mean the following:

"Hydrocarbyl" and "hydrocarbylene" embrace moieties consisting exclusively of the elements carbon and hydrogen, which may optionally be substituted with other hydrocarbon, halo (e.g., chlorine, fluorine, bromine, iodine) or hetero (e.g., nitrogen, oxygen, sulfur) substituents. These moieties include alkyl, alkenyl, alkynyl and aryl moieties, as well as alkyl, alkenyl, alkynyl and aryl moieties substituted with other aliphatic or cyclic hydrocarbon groups such as, for example, alkaryl, alkenaryl and alkynaryl.

The alkyl groups described herein are preferably lower alkyl containing from about 1 to about 20 carbon atoms in the principal chain, although 40, 80 or even 100 carbon atoms may be present in some cases. The alkyl groups may be a straight or branched chains and include methyl, ethyl, propyl, isopropyl, butyl, isobutyl, tertiary butyl, pentyl, hexyl and the like. They may be substituted with aliphatic or cyclic hydrocarbon radicals, halogens, or hetero-substituted with the various substituents (e.g., oxygen, nitrogen, sulfur, etc.) defined herein.

The alkenyl groups described herein are preferably lower alkenyl containing from about 2 to about 20 carbon atoms in the principal chain, although 40, 80 or even 100 carbon atoms may be present in some cases. They may be straight or branched chains and include ethenyl, propenyl, isopropenyl, butenyl, isobutenyl, pentenyl, hexenyl, and the like. They may be substituted with aliphatic or cyclic hydrocarbon radicals, halogens, or hetero-substituted with the various substituents (e.g., oxygen, nitrogen, sulfur, etc.) defined herein.

The alkynyl groups described herein are preferably lower alkynyl containing from about 2 to about 20 carbon atoms in the principal chain, although 40, 80 or even 100 carbon atoms may be present in some cases. They may be straight or branched chain and include ethynyl, propynyl, butynyl, isobutynyl, pentynyl, hexynyl, and the like. They may be substituted with aliphatic or cyclic hydrocarbon radicals, halogens, or hetero-substituted with the various substituents (e.g., oxygen, nitrogen, sulfur, etc.) defined herein.

The term "heteroalkyl" refers to an alkyl radical or substituent as described above in which one or more carbon atoms of the main chain of the alkyl radical is replaced by a heteroatom, such as nitrogen, oxygen, phosphorus, sulfur, etc.

The term "cycloalkyl" is used herein to refer to a saturated or unsaturated cyclic, non-aromatic hydrocarbon radical having a single ring or multiple condensed rings. Suitable cycloalkyl radicals include, for example, cycloalkyls have between 3 and 20 carbon atoms.

"Substituted cycloalkyl" refers to a cycloalkyl radical or substituent as described herein in which one or more hydrogen atoms bound to any carbon of the cycloalkyl radical is replaced by another group such as a heteroatom, halogen, alkyl, substituted alkyl, aryl, substituted aryl, cycloalkyl, substituted cycloalkyl, heterocycloalkyl, substituted heterocycloalkyl, heteroaryl, substituted heteroaryl, and combinations thereof.

The term "heterocycloalkyl" is used herein to refer to a cycloalkyl radical as described herein in which one or more of the carbon atoms of the saturated or unsaturated cyclic radical are replaced by a heteroatom, such as nitrogen, phosphorus, oxygen, sulfur, etc.

"Substituted heterocycloalkyl" refers to a heterocycloalkyl radical as described herein in which one or more hydrogen atoms bound to any atom of the heterocycloalkyl radical is replaced by another group such as a halogen, alkyl, substituted alkyl, aryl, substituted aryl, heteroaryl, substituted heteroaryl and combinations thereof.

The term "aryl" is used herein to refer to an aromatic radical or substituent which may be a single aromatic ring or multiple aromatic rings which are fused together, linked covalently, or linked to a common group such as a methylene or ethylene moiety. The aromatic ring(s) may include phenyl, naphthyl and biphenyl, among others. In particular embodiments, aryls have between 1 and 20 carbon atoms.

"Substituted aryl" refers to an aryl radical as described above in which one or more hydrogen atoms bound to any carbon is replaced by one or more functional groups such as alkyl, substituted alkyl, cycloalkyl, substituted cycloalkyl, heterocycloalkyl, substituted heterocycloalkyl, halogen, alkylhalos (e.g., CF$_3$), and both saturated and unsaturated cyclic hydrocarbons which are fused to the aromatic ring(s), linked covalently or linked to a common group such as a methylene or ethylene moiety. The common linking group may also be a carbonyl, as in benzophenone, or oxygen, as in diphenylether, or nitrogen, as in diphenylamine.

The term "heteroaryl" as used herein refers to an aromatic ring substituent or radical in which one or more carbon atoms of the aromatic ring(s) is/are replaced by a heteroatom, such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group, such as a methylene or ethylene moiety. The common linking group may also be a carbonyl, as in phenyl pyridyl ketone. As used herein, rings such as thiophene, pyridine, isoxazole, phthalimide, pyrazole, indole, furan, etc., or benzo-fused analogues of these rings, are defined by the term "heteroaryl."

"Substituted heteroaryl" refers to a heteroaryl radical as described above in which one or more hydrogen atoms bound to any atom of the heteroaryl moiety is replaced by another group such as a halogen, alkyl, substituted alkyl, aryl, substituted aryl, heteroaryl, substituted heteroaryl, amino and combinations thereof.

"Contacting" a reactant POM, amine, diimide, and optionally a solvent (or, alternatively, a reactant POM, an amino-substituted diimide and optionally a solvent) is intended to refer generally to the various ways by which the components of, for example, the reacting mixture are brought together, such that a reaction occurs, including for example: (i) bringing the reactant POM and amine, and optionally the solvent, into contact with each other and then supplying the diimide; (ii) bringing the POM and the diimide, and optionally the solvent, into contact with each other and then supplying the amine; or (iii) bringing the amine and diimide, and optionally the solvent, into contact with each other, and then supplying the POM.

A "corresponding" POM, or alternatively amine, is intended to generally denote the structural relationship between a given POM to be substituted and the desired substituted POM product resulting therefrom, or similarly the amine from which the amine substituent is derived; that is, a "corresponding" reactant POM or amine and substituted POM product and amine substituent are structurally the same, with the exception that the product POM has an amine functionality or substituent, which has replaced a "leaving group" from the POM (e.g., an oxygen atom), and the amine substituent is attached to the POM rather than one or more hydrogen atoms, for example.

"Average composition," as used herein with reference to the polyoxometalate, the substituted polyoxometalate, or the anion thereof, is intended to address the fact that, when formed, these metal oxides can exist as mixtures of various forms (i.e., various ratios of, for example, (i) metal to oxygen or, if a combination of metals ("M"), or metals with non-metals other than oxygen ("NM"), is used, (ii) from $M^1$ to $M^2$ or from $M^1$ to $NM^1$, or (iii) anion composition to counter cation). Accordingly, "average composition" refers to the average composition of the polyoxometalate, adjusted to the nearest stoichiometric balance.

"Amine-derived substituent," as used herein in the context of, for example, a substituted POM, generally refers to any substituent bound to the POM by means of a metal-nitrogen bond, including a single bond (sometimes referred to herein as amino-substituted or substituent), a double bond (sometimes referred to herein as imido-substituted or substitutent), or a triple bond.

The processes of the present invention are further illustrated by the following Examples. The Examples are designed to illustrate to those of ordinary skill in the art how to practice the processes of the invention. These are therefore not to be interpreted in a limiting sense.

EXAMPLES

Example 1

Reaction Time/Yield Study

To study the relationship between reaction time, reaction yield and the number of diimide equivalents used in the present process, a series of reactions were carried out, wherein various amounts of dicyclohexylcarbodiimide (DCC) were reacted with $[Mo_6O_{19}]^{-2}$ and 2,6-dimethylaniline in refluxing acetonitrile. Referring now to FIG. 1, it can be seen that when 0.5 equivalents of DCC were used, a yield close to 50% was obtained after about 18 hours. If 1 equivalent was used, a yield of about 93% was obtained after allowing the reaction to proceed for about 12 hours.

In contrast, it was observed that when no DCC was used, no reaction occurred, even after allowing the reaction to proceed at reflux for more than two days and adding triethylamine (a reported catalyst for such a reaction). Additionally, it was observed that when more than 1 equivalent was used, the reaction proceeded even faster, but the reaction yield decreased. As illustrated in FIG. 1, as the reaction time increased, the reaction yield increased initially, but eventually reached a maximum and then decreased. For example, when the addition of about 4 equivalents of DCC, the highest yield observed was only about 33%, which was reached in about 3 hours. In addition, no reaction product was isolated after 6 hours.

Example 2

Preparation of Functionalized POMs

The synthetic procedure for the reaction of a hexamolybdate anion with arylamine is exemplified by the following synthesis of compound 1 (the structure of which is presented herein above): A mixture of 2,6-dimethyl-4-iodoaniline (1.052 mmol), dicyclohexylcarbodiimide (1.134 mmol) and $[Bu_4N]_2[Mo_6O_{19}]$ (1.064 mmol) was refluxed in 20 ml of acetonitrile under nitrogen for about 12 hours. After being cooled to room temperature, the resulting red-orange solution was filtered to remove the white precipitates (N,N'-dicyclohexylurea). Absolute ethanol (20 ml) was then added in the filtrate. The reaction product precipitated out of the solution as orange crystals. The product was then collected by filtration, washed successively with EtOH and $Et_2O$ several times, and dried under vacuum to yield Compound 1. (72% yield) Anal. Calc'd. $C_{40}H_{80}N_3O_{18}IMo_6$ (%): C, 30.15; H, 5.06; N, 2.64. Found: C, 30.40; H, 4.98; N, 2.64. $^1H$ NMR ($d_6$-acetone, ppm): δ7.45 (s, ArH, 2H), 3.45 (t, J=8.63 Hz, $NCH_2$, 16H), 2.58 (s, (Ar—)$CH_3$, 6H), 1.82 (q, J=7.94 Hz, $CH_2$, 16H), 1.46 (sextet, J=7.25 Hz, $CH_2$, 16H), 0.98 (t, J=7.25 Hz, $CH_3$, 24H). UV-Vis [MeCN; λ/nm (ε/$M^{-1}$ $cm^{-1}$)]: 204 (5.0×10$^4$), 246 (3.7×10$^4$), 364 (2.6×10$^4$). (The chemical structure was confirmed by X-ray single crystal analysis.)

Following the above-described procedure (i.e., regents, ratios, reaction conditions, etc.), Compounds 2 and 3 were also prepared, the results being as follows:

Compound 2 (yield, 91%). Anal. Calc'd. $C_{42}H_{81}N_3O_{18}Mo_6$ (%): C, 33.82; H, 5.47; N, 2.82. Found: C, 33.32; H, 5.24; N, 2.75. $^1H$ NMR ($d_6$-acetone, ppm): δ7.17 (s, ArH, 2H), 3.65 (s, C=CH, 1H), 3.44 (t, J=8.63 Hz, $NCH_2$, 16H), 2.60 (s, (Ar—)$CH_3$, 6H), 1.82 (q, J=7.90 Hz, $CH_2$, 16H), 1.46 (H, J=7.25 Hz, $CH_2$, 16H), 0.99 (t, J=7.25 Hz, $CH_3$, 24H). UV/Vis [MeCN; λ/nm (ε/$M^{-1}$ $cm^{-1}$)]: 206 (5.4×10$^4$), 264 (4.1×10$^4$), 368 (2.8×10$^4$). (The structure is confirmed by X-ray single crystal analysis.)

Compound 3 (yield, 25%). $^1H$ NMR ($d_3$-acetonitrile, ppm): δ7.47 (s, $C_6H_2$ (m), 4), 3.81 (m, J=7.50 Hz, (Ar—)$CHMe_2$, 6H), 3.10 (t, J=8.50 Hz, $NCH_2$, 16H), 1.60 (q, J=8.50 Hz, $CH_2$, 16H), 1.35 (H, J=8.50 Hz, $CH_2$, 16H), 1.25 (d, J=6.25 Hz, $CH_3$ of (Ar—)$CHMe_2$, 24H), 0.96 (t, J=7.25 Hz, $CH_3$, 24H). (The structure is confirmed by X-ray single crystal analysis.)

In addition to the above, Compounds 6 and 7 were prepared as follow:

Compound 6:

A mixture of 4-iodo-2,6-diisopropylaniline (0.63 g, 2.1 mmol), dicyclohexylcarbodiimide (0.44 g, 2.1 mmol) and $[Bu_4N]_2[Mo_6O_{19}]^{2-}$ (1.36 g, 1.0 mmol) was refluxed in acetonitrile (25 mL) under $N_2$ for about 24 hours. After cooling to room temperature, the resulting red-orange solution was filtered to remove the white solid (N,N'-dicyclohexylurea). Absolute ethanol (20 ml) was then added into the filtrate. The product precipitates out of the solution as orange crystals. The product was collected by filtration, washed successively with EtOH and $Et_2O$ for several times, and then recrystallized three time from hot acetonitrile to yield 1.10 g (56%) of purified X-ray quality block-like red crystals. Anal. Calc'd. for $C_{56}H_{104}N_4O_{17}Mo_6$ (%): C, 34.76; H, 5.42; N, 2.90. Found: C, 34.60; H, 5.61; N, 2.83. $^1$H NMR ($d_3$-acetonitrile, ppm): δ7.47 (s, $C_6H_2$ (m), 4), 3.81 (m, J=7.50 Hz, (Ar—)$CHMe_2$, 6H), 3.10 (t, J=8.50 Hz, $NCH_2$, 16H) 1.60 (q, J=8.50 Hz, $CH_2$, 16H), 1.35 (H, J=8.50 Hz, $CH_2$, 16H), 1.25 (d, J=6.25 Hz, $CH_3$ of (Ar—)$CHMe_2$, 24H), 0.96 (t, J=7.25 Hz, $CH_3$, 24H). (The structure is confirmed by X-ray single crystal analysis.)

Compound 7: To begin, first the mixed-metal POM of tungsten and molybdenum, $[W_5MoO_{19}]^{2-}$, was prepared as follows: The mixture of $[Bu_4N]_4[W_{10}O_{32}]$ (29.40 g, 8.85 mmol) and $[Bu_4N]_2[Mo_2O_7]$ (7.99 g, 10.13 mmol) was refluxed in methanol (30 ml)/acetonitrile (60 ml) under $N_2$ for 4 to 6 hours. After cooling to room temperature, the resulting yellow-green solution was filtered to remove the white precipitates. The filtrate was allowed to stand undisturbed for 6 to 8 hours, and the product crystallized from the solution as yellowish block-like crystals. Further re-crystallization from acetone yielded analytically pure products (16.6 g, 52%). Compound 7: The mixture of 4-iodo-2,6-dimethylaniline (0.24 g, 0.97 mmol), dicyclohexyl-carbodiimide (0.30 g, 1.46 mmol) and $[Bu_4N]_2[MoW_5O_{19}]$ (1.90 g, 1.05 mmol) was refluxed in acetonitrile (10 mL) under $N_2$ for about 12 hours. After cooling to room temperature, the resulting red-brown solution was filtered to remove the white precipitates (i.e., dicyclohexylurea). Absolute ethanol (20 ml) was then added into the filtrate. As solvents evaporate, colorless crystals of $[Bu_4N]_2[W_6O_{19}]$ precipitate first from the solution and was removed by filtration. The product then crystallized out of solution upon further evaporation of solvents as brown crystals. The product was further purified by recrystallization from acetone/ethanol and dried under vacuum (1.30 g, 64% yield). Anal. Calc'd. $C_{41}H_{83}N_3O_{19.5}IMoW_5$ (%): C, 23.95; H, 4.07; N, 2.19. Found: C, 24.28; H, 3.56; N, 2.10. $^1$H NMR ($d_6$-acetone, ppm): δ7.50 (s, $C_6H_3$ (m), 2H), 3.46(t, J=8.50 Hz, $NCH_2$, 16H), 2.62 (s, (Ar—)$CH_3$, 6H), 1.84(q, J=7.25 Hz, $CH_2$, 16H), 1.46 (H, J=7.25 Hz, $CH_2$, 16H), 0.99(t, J=7.25 Hz, $CH_3$, 24H). UV-Vis [MeCN; λ/nm (ε/$M^{-1}$ $cm^{-1}$)]: 202 (4.71×10$^4$), 248 (3.52×10$^4$), 356 (2.60×10$^4$). (The structure is confirmed by X-ray single crystal analysis.)

Example 3

Coupling of Functionalized POM and Ethynylarene

The Pd-catalyzed coupling reaction between an iodo-functionalized POM and an ethynylarene is exemplified by the following synthesis of Compounds 15 and 16 (the structures of which are presented herein above): Two mixtures were prepared, each containing Compound 1 (i.e., $(Mo_6O_{18}=N-C_6H_2(CH_3)_2-I$, 2.00 g, 1.26 mmol), $Pd(PPh_3)_2Cl_2$ (0.026 g, 0.03 equiv.), CuI (0.014 g, 0.06 equiv.), triethylamine (1 g), and 1.90 mmol (1.5 equiv.) of either 1-ethynyl-3,5-di(t-butyl)benzene (for Compound 16) or 1-ethynyl-4-methylbenzene (for Compound 15), and stirred in acetonitrile (40 mL) at room temperature for 20 minutes, leading to the formation of shiny red solutions.

$CH_2Cl_2$ (100 mL) was added to each solution, and then each of the resulting solutions was washed twice with $H_2O$ and brine water, after which they were each concentrated to about 10 mL. After the addition of 200 mL of hexane to each of the above concentrated solutions, they was left standing for 2 hours. The top, yellowish clear solution was discarded. The oily dark red residue was dried under vacuum to yield the products as dark red solids (Compound 15, 85% yield; Compound 16, 72% yield).

Compound 15: Anal. Calc'd. for $C_{56}H_{101}N_3O_{18}Mo_6$ (%): C, 40.04; H, 6.06; N, 2.51. Found: C, 40.99; H, 6.07; N, 2.55. $^1$H NMR (250 MHz, [$D_6$]acetone, 25° C., TMS): δ0.97 (t, J=7.25 Hz, 24H, —$CH_3$), 1.34 (s, 18H, —$C(CH_3)_3$), 1.47 (sextet, J=7.30 Hz, 16H, —$CH_2$—), 1.83 (quintet, J=7.94 Hz, 16H, —$CH_2$—), 2.64 (s, 6H, Ar—H), 3.45 (t, J=8.50 Hz, 16H, N—$CH_2$), 7.25 (s, 2H, Ar—H), 7.39 (s, 2H, Ar—H), 7.52 (s, 2H, Ar—H). (The structure is confirmed by X-ray single crystal analysis.)

Compound 16: Anal. Calc'd. for $C_{49}H_{87}N_3O_{18}Mo_6$ (%): C, 37.21; H, 5.54; N, 2.66. Found: C, 36.83; H, 5.32; N, 2.61. $^1$H NMR (250 MHz, [$D_6$]acetone, 25° C., TMS): δ0.99 (t, J=7.38 Hz, 24H, —$CH_3$), 1.46 (sextet, J=7.3 Hz, 16H, —$CH_2$—), 1.83 (quintet, J=7.94 Hz, 16H, —$CH_2$), 2.37 (s, 3H, Ar—H), 3.47 (t, J=8.5 Hz, 16H, N—$CH_2$—), 7.23 (s, 2H, Ar—H), 7.25 (d, J=8.5 Hz, 2H, Ar—H), 7.42 (d, J=7.25 Hz, 2H, Ar—H). (The structure is confirmed by X-ray single crystal analysis.)

This example illustrates one advantage of the present invention, in that the reaction proceeds quickly (taking only a few minutes) and with high yield. Additionally, the reaction products were found to be readily soluble in common organic solvents, including methylene chloride, chloroform, acetone, acetonitrile, tetrahydrofuran (THF) and dimethylformamide (DMF). Finally, the reaction products were found to exhibit excellent stability when exposed to oxygen and moisture, no obvious signs of decomposition being observed after solutions of these compounds were allowed to stand in air for about one month.

Example 4

Coupling of Functionalized POMs

The Pd-catalyzed coupling reaction between a dimethyl-iodoaniline functionalized POM and a dimethyl-ethynylaniline functionalized POM is exemplified by the following synthesis of compounds 17 and 18 (the structures of which are presented herein above):

Compound 17: A mixture of Compound 1 (0.75 g, 0.5 mmol), Compound 2 (0.80 g, 0.5 mmol), $Pd(PPh_3)_2Cl_2$ (10 mg, 0.01 mmol), copper (I) iodide (6 mg, 0.02 mmol), $K_2CO_3$ (anhydrous, 1.0 g, 7 mmol), triethylamine in acetonitrile (0.5 mL of 1M solution, 0.5 mmol) and acetonitrile (20 mL) was stirred at room temperature for about 30 min under nitrogen. The resulting dark-red solution was added to 100 mL of $CH_2Cl_2$, washed twice with brine water, and then concentrated to about 30 mL. After the addition of 100 mL of ethyl ester, the solution was left standing without disturbance for about 8 h. The orange precipitate was collected by filtration and washed successively with methylene chloride and acetone. It was further purified by recrystallizing twice with acetone, yielding 1.16 g of the title compound (78%). The compound was found to be only slightly soluble in solvents such as acetone, acetonitrile, methylene chloride and chloroform.

The single crystals used for X-ray diffraction were obtained by the diffusion of ethyl ester into a solution of Compound 17 in DMF. Anal. Calc'd. for $C_{82}H_{160}N_6O_{36}Mo_{12}$ (%): C, 33.30; H, 5.45; N, 2.84. Found: C, 33.06; H, 5.53; N, 2.80. $^1$H NMR (250 MHz, [D$_3$]MeCN, 25° C., TMS): δ=7.22 (s, aromatic protons, 4H), 3.09 (t, J=8.50 Hz, NCH$_2$, 32H), 2.59 (s, (Ar—)CH$_3$, 12H), 1.60 (q, J=7.94 Hz, CH$_2$, 32H), 1.35 (H, J=7.25 Hz, CH$_2$, 32H), 0.96 (t, J=7.25 Hz, CH$_3$, 48H) UV-Vis (MeCN): λ/nm (ε/M$^{-1}$ cm$^{-1}$)=206 (1.40×10$^5$), 260 (9.43×10$^4$), 426 (1.04×10$^5$). (The structure is confirmed by X-ray single crystal analysis.)

Compound 18: A mixture of 2,5-di(2,2-dimethyl-propyloxy)-1,4-diethynylbenzene (0.5 mmol), two equivalents of Compound 1 (1.75 g, 1.1 mmol), Pd(PPh$_3$)$_2$Cl$_2$ (40 mg, 0.057 mmol), copper (I) iodide (20 mg, 0.1 mmol), triethylamine (1 mL) and acetonitrile (40 mL) was stirred, under the protection of nitrogen for 1 h at room temperature. The dark-red solution was added to 300 mL of CH$_2$Cl$_2$ and washed twice with water. The organic layer was collected and the solvent was then removed by vacuum evaporation. To the residue was added 20 mL of acetone. The resulting suspension was filtered through a syringe filter (0.2 μm), and the filtrate was concentrated to about 10 mL. The concentrated solution was added slowly to 200 mL of diethyl ether. After standing for 10 minutes, the top layer of solvents was decanted. The oily residue was dried under vacuum overnight to give a dark red powder, which was purified by recrystallizing with acetone/ethyl ether to yield an analytically pure product (81%). The compound was found to be readily soluble in solvents such as acetone, acetonitrile, methylene chloride and chloroform.

Anal. Calc'd. for $C_{100}H_{182}N_6O_{38}Mo_{12}$ (%): C, 37.21; H, 5.68; N, 2.60. Found: C, 37.60; H, 5.24; N, 2.33. $^1$H NMR (400 MHz, [D$_3$]MeCN, 25° C.): δ=0.96 (t, J=7.25 Hz, 48H, —CH$_3$), 1.09 (s, 18H, —CH$_3$), 1.35 (m, 32H, —CH$_2$—), 1.59 (m, 32H, —CH$_2$—), 2.60 (S, 12H, ArCH$_3$), 3.10 (m, 32H, NCH$_2$—), 3.71 (s, 4H, OCH$_2$—), 7.05 (s, 2H, Ar—H), 7.21 (s, 4H, Ar—H). $^{13}$C NMR (400 MHz, [D$_3$]MeCN, 25° C.): δ=14.2, 18.8, 20.7, 24.7, 27.2, 33.2, 59.6, 80.4, 89.7, 95.9, 114.9, 123.4, 131.2, 139.7, 154.6, 155.3. UV-Vis (MeCN): λ$_{max}$/nm (ε/M$^{-1}$ cm$^{-1}$)=206 (1.36×10$^5$), 250 (8.82×10$^4$), 438 (1.24×10$^5$).

In view of the above, it will be seen that the several objects and features of the invention are illustrated and achieved. As various changes could be made in the above-described process and compounds without departing from the scope of the present invention, it is intended that all matter contained in the above description shall be interpreted as illustrative and not in a limiting sense.

What is claimed is:

1. A process for preparing a polyoxometalate having an amine-derived substituent attached thereto, the process comprising contacting a polyoxometalate and an amine in the presence of a diimide.

2. The process of claim 1 wherein the amine is a primary amine.

3. The process of claim 2 wherein the diimide is a carbodiimide.

4. The process of claim 3 wherein the polyoxometalate comprises molybdenum.

5. The process of claim 4 wherein the polyoxometalate, the amine, the diimide and a solvent are contacted in a reaction zone to form a reacting mixture.

6. The process of claim 5 wherein the solvent is a polar, aprotic solvent.

7. The process of claim 6 wherein the polar, aprotic solvent is selected from acetonitrile, pyridine, benzonitrile and N,N-dimethylformamide.

8. The process of claim 5 wherein the reaction is conducted at a temperature ranging from greater than about 25° C. to about 150° C.

9. The process of claim 5 wherein the reaction is conducted at a temperature ranging from greater than about 50° C. to about 125° C.

10. The process of claim 5 wherein the reacting mixture is heated to about the reflux temperature.

11. The process of claim 5 wherein the reacting mixture is heated for about 1 hour to less than about 48 hours.

12. The process of claim 5 wherein the reacting mixture is heated for about 4 hours to less than about 24 hours.

13. The process of claim 5 wherein the reacting mixture is heated for about 8 hours to less than about 12 hours.

14. The process of claim 5 wherein the reaction proceeds under atmospheric pressure or greater.

15. The process of claim 14 wherein the reaction proceeds in the presence of air.

16. The process of claim 14 wherein the reaction proceeds under an inert atmosphere.

17. The process of claim 5 wherein the reaction proceeds under anhydrous conditions.

18. The process of claim 1 wherein a yield of the substituted polyoxometalate is at least about 50%.

19. The process of claim 1 wherein a yield of the substituted polyoxometalate is at least about 75%.

20. The process of claim 1 wherein the molar ratio of diimide to polyoxometalate ranges from about 20:1 to about 1:2.

21. The process of claim 1 wherein the molar ratio of diimide to polyoxometalate ranges from about 2:1 to about 1:1.

22. The process of claim 1 wherein the molar ratio of amine to polyoxometalate ranges from about 20:1 to about 1:2.

23. The process of claim 1 wherein the molar ratio of amine to polyoxometalate ranges from about 2:1 to about 1:1.

24. The process of claim 1 wherein the molar ratio of diimide to amine is at least about 1:1.

25. The process of claim 1 wherein the molar ratio of diimide to amine is at least about 1.5:1.

26. The process of claim 1 wherein the molar ratio of diimide to amine to polyoxometalate is about 1.5:1:1.

27. The process of claim 1 wherein the molar ratio of diimide to amine to polyoxometalate is about 1:1:1.

28. The process of claim 1 wherein the substituted polyoxometalate has the formula:

$$\left[(M_aO_{b-d})\text{-}(\text{-}NR^1R^2)_d\right]^q \quad \text{or} \quad \left[(M_aO_{b-d})\text{-}(\text{-}NR^1)_d\right]^q$$

wherein:

($M_aO_{b-d}$) represents the composition of the metal-oxygen cluster portion of the substituted polyoxometalate, the substituted polyoxometalate comprising one or more metals, M, which may be the same or different, selected from molybdenum, tungsten, vanadium, niobium, tantalum or a combination thereof; and, O is oxygen;

N is nitrogen;

$R^1$ is a substituent selected from substituted or unsubstituted hydrocarbyl or substituted or unsubstituted heterohydrocarbyl;

$R^2$ is a substituent selected from hydrogen, substituted or unsubstituted hydrocarbyl or substituted or unsubstituted heterohydrocarbyl;

a represents the number of metal atoms;

d represents the number of amine-derived substituents on the polyoxometalate;

b–d represents the number of oxygen atoms, the number of oxygen atoms decreasing as the number of amine-derived substituents increases; and, q represents the net charge of the substituted polyoxometalate.

29. The process of claim 28 wherein a ranges from about 6 to about 18.

30. The process of claim 29 wherein d ranges from about 1 to about 18.

31. The process of claim 30 wherein b ranges from about 19 to about 62.

32. The process of claim 29 wherein a is 6, b is 19 and d ranges from about 1 to about 6.

33. The process of claim 32 wherein at least one metal of the polyoxometalate is molybdenum.

34. The process of claim 29 wherein a is 7, b is 23 and d ranges from about 1 to about 7.

35. The process of claim 34 wherein at least one metal of the polyoxometalate is molybdenum.

36. The process of claim 28 wherein the diimide is a carbodiimide.

37. The process of claim 36 wherein the carbodiimide is selected from diethylcarbodiimide, diisopropylcarbodiimide and dicyclohexylcarbodiimide.

38. The process of claim 28 wherein $R^1$ is selected from the group consisting of substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted allyl, substituted or unsubstituted aryl, substituted or unsubstituted heteroaryl, or a combination thereof.

39. The process of claim 38 wherein $R^1$ is substituted or unsubstituted alkyl having about 1 to about 20 carbon atoms in the main chain.

40. The process of claim 39 wherein $R^1$ is substituted or unsubstituted methyl, ethyl, propyl, i-propyl, butyl, t-butyl, pentyl, or hexyl.

41. The process of claim 38 wherein $R^1$ is substituted or unsubstituted aryl or heteroaryl.

42. The process of claim 41 wherein $R^1$ is halo-substituted aryl.

43. The process of claim 42 wherein $R^1$ is halo-substituted phenyl.

44. The process of claim 43 wherein $R^1$ is iodo-substituted phenyl.

45. The process of claim 41 wherein $R^1$ is alkynyl-substituted aryl.

46. The process of claim 45 wherein $R^1$ is alkynyl-substituted phenyl.

47. The process of claim 46 wherein $R^1$ is ethynyl-substituted phenyl.

48. The process of claim 1 wherein the substituted polyoxometalate has an average composition represented by the structure:

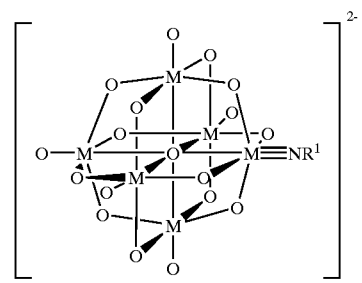

wherein M is a metal selected from the group consisting of molybdenum, tungsten, vanadium, niobium, tantalum, or a combination thereof, provided at least one of the metal atoms is molybdenum, N is nitrogen, O is oxygen and $R^1$ a substituent selected from the group consisting of substituted or unsubstituted hydrocarbyl.

49. The process of claim 48 where each M is molybdenum.

50. The process of claim 48 where M is a combination of molybdenum and tungsten.

51. An arylamino-substituted polyoxometalate compound having an average composition of the formula:

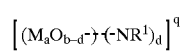

wherein:

$(M_aO_{b-d})$ represents the average composition of the metal-oxygen cluster portion of the substituted polyoxometalate, the substituted polyoxometalate comprising one or more metals, M, which may be the same or different, selected from molybdenum, tungsten, vanadium, niobium, tantalum or a combination thereof; and, O is oxygen;

N is nitrogen;

$R^1$ is a substituent selected from the group consisting of substituted or unsubstituted iodoarylene, alkynylarylene, N-alkylaminoarylene and N,N-dialkylaminoarylene;

a represents the number of metal atoms;

d represents the number of amine-derived substituents on the polyoxometalate;

b–d represents the number of oxygen atoms, the number of oxygen atoms decreasing as the number of amine-derived substituents increases; and, q represents the net charge of the substituted polyoxometalate.

52. The compound of claim 51 wherein $R^1$ is iodophenylene.

53. The compound of claim 51 wherein $R^1$ is ethynylphenylene.

54. The compound of claim 51 wherein $R^1$ is N,N-diethylaminophenylene.

55. The compound of claim 51 wherein M is molybdenum, tungsten or a combination thereof.

56. The compound of claim 55 wherein said compound is capable of forming an anion selected from the group consisting of:

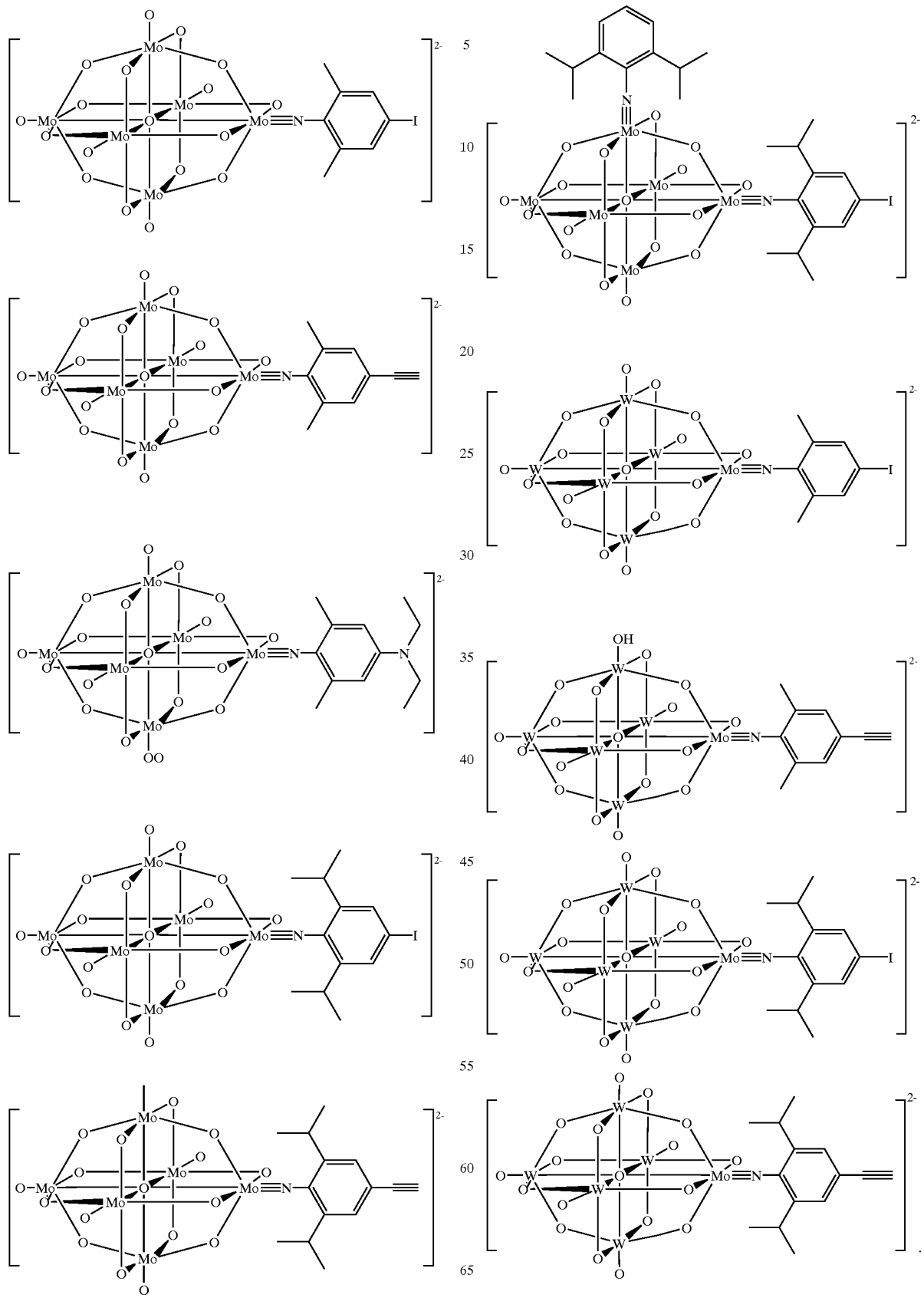

57. A process for preparing a substituted polyoxometalate reaction product, the process comprising contacting, in the presence of a catalyst capable of catalyzing a coupling reaction between a halo-substituted compound and a compound having an unsaturated bond therein, a first reactant polyoxometalate having a substituent bound thereto selected from a halo-substituted hydrocarbyl or a hydrocarbyl having an unsaturated bond therein, with a second reactant compound comprising a halo substituent or an unsaturated bond, with the proviso that when the first reactant polyoxometalate is halo-substituted the second reactant compound comprises an unsaturated bond or vice versa.

58. The process of claim 57 wherein the first reactant polyoxometalate is halo-substituted.

59. The process of claim 57 wherein the first reactant polyoxometalate is iodo-substituted.

60. The process of claim 59 wherein the second reactant compound is a substituted or unsubstituted alkene or alkyne.

61. The process of claim 59 wherein the second reactant compound is a substituted polyoxometalate, said second reactant polyoxometalate having an alkenyl or alkynyl substituent bound thereto, the reaction product being a bridged polyoxometalate.

62. The process of claim 57 wherein the second reactant compound is halo-substituted.

63. The process of claim 62 wherein the second reactant compound is iodo-substituted.

64. The process of claim 62 wherein the first reactant polyoxometalate has a substituent selected from substituted or unsubstituted alkenyl or substituted or unsubstituted alkynyl.

65. The process of claim 62 wherein the second reactant compound is a substituted polyoxometalate, the reaction product being a bridged polyoxometalate.

66. The process of claim 57 wherein the first reactant polyoxometalate has the formula

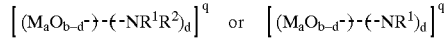

wherein:
($M_aO_{b-d}$) represent a metal-oxygen cluster, M being one or more metals, which may be the same or different, selected from molybdenum, tungsten, vanadium, niobium, tantalum or a combination thereof, and O being oxygen;

N is nitrogen;

$R^1$ is a substituent comprising a halogen or an unsaturated bond;

$R^2$ is a substituent selected from hydrogen, substituted or unsubstituted hydrocarbyl or substituted or unsubstituted heterohydrocarbyl;

a represents the number of metal atoms;

d represents the number of amine-derived substituents on the metal-oxygen cluster;

b–d represents the number of oxygen atoms in the metal-oxygen cluster, the number of oxygen atoms decreasing as the number of amine-derived substituents increases; and, q represents the net charge of the first reactant polyoxometalate.

67. The process of claim 57 wherein the coupling catalyst comprises palladium.

68. The process of claim 67 wherein the palladium coupling catalyst is $Pd(PPh_3)_2Cl_2$.

69. A process for preparing a bridged polyoxometalate reaction product, wherein two or more metal-oxygen clusters are linked, the process comprising contacting a first reactant polyoxometalate and a second reactant polyoxometalate, each having a substituent which does not comprises a metal-oxygen bond with the reactant polyoxometalate, the substituent on the first reactant polyoxometalate being different from the substituent on the second reactant polyoxometalate, the two reactant polyoxometalates being contacted in the presence of a catalyst capable of catalyzing a coupling reaction between the two different substituents.

70. The process of claim 69 wherein the first reactant polyoxometalate and the second reactant polyoxometalate have different amine-derived substituents bound thereto via a metal-nitrogen bond.

71. The process of claim 70 wherein the first reactant polyoxometalate comprises a substituted or unsubstituted haloarylamine-derived substituent.

72. The process of claim 71 wherein the second reactant polyoxometalate comprises a substituted or unsubstituted alkenylarylamine-derived substituent or a substituted or unsubstituted alkynylarylamine-derived substituent.

73. The process of claim 72 wherein the coupling catalyst comprises palladium.

74. The process of claim 73 wherein the palladium coupling catalyst is $Pd(PPh_3)_2Cl_2$.

75. The process of claim 72 wherein the second reactant polyoxometalate comprises a substituted or unsubstituted ethynylphenylamine-derived substituent or a substituted or unsubstituted ethenylphenylamine-derived substituent.

76. The process of claim 75 wherein the first reactant polyoxometalate comprises a substituted or unsubstituted iodophenylamine-derived substituent.

77. A process for preparing a polyoxometalate having an amine-derived substituent attached thereto, the process comprising contacting a reactant polyoxometalate, a reactant primary or secondary amine, and a reactant activating compound which bonds with a terminal oxygen of the reactant polyoxometalate, forming a leaving group therewith.

78. The process of claim 77 wherein the amine is a primary amine.

79. The process of claim 72 wherein the reactant activating compound is a diimide.

80. The process of claim 79 wherein the diimide is a carbodiimide.

81. The process of claim 77 wherein the reactant polyoxometalate comprises molybdenum.

82. The process of claim 77 wherein the reactant polyoxometalate, the reactant amine, the reactant activating compound and a solvent are contacted in a reaction zone to form a reacting mixture.

83. The process of claim 82 wherein the reaction is conducted at a temperature ranging from greater than about 25° C. to about 150° C.

84. The process of claim 82 wherein the reacting mixture is heated for about 4 hours to less than about 24 hours.

85. The process of claim 82 wherein the reaction proceeds under an inert atmosphere.

86. The process of claim 77 wherein a yield of the substituted polyoxometalate is at least about 75%.

87. The process of claim 77 wherein the molar ratio of reactant activating compound to reactant polyoxometalate ranges from about 20:1 to about 1:1.

88. The process of claim 77 wherein the molar ratio of reactant amine to reactant polyoxometalate ranges from about 20:1 to about 1:1.

89. The process of claim 77 wherein the molar ratio of reactant activating compound to reactant amine to reactant polyoxometalate is about 1:1:1.

90. A process for preparing a polyoxometalate having an amine-derived substituent bound thereto, the process comprising contacting a polyoxometalate and an amino-substituted diimide.

91. The process of claim 90 wherein the amine substituent on the diimide is a primary amine.

92. The process of claim 90 wherein the amino-substituted diimide is an amino-substituted carbodiimide.

93. The process of claim 90 wherein the polyoxometalate comprises molybdenum.

94. The process of claim 90 wherein the polyoxometalate, the amino-substituted diimide and a solvent are contacted in a reaction zone to form a reacting mixture.

95. The process of claim 94 wherein the reaction is conducted at a temperature ranging from greater than about 25° C. to about 150° C.

96. The process of claim 94 wherein the reacting mixture is heated for about 4 hours to less than about 24 hours.

97. The process of claim 94 wherein the reaction proceeds under an inert atmosphere.

98. The process of claim 90 wherein a yield of the substituted polyoxometalate is at least about 75%.

99. The process of claim 90 wherein the molar ratio of amino-substituted diimide to polyoxometalate ranges from about 20:1 to about 1:1.

100. The process of claim 99 wherein the molar ratio amino-substituted diimide to polyoxometalate is about 1:1.

101. The process of claim 90 wherein the substituted polyoxometalate has the formula:

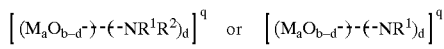

wherein:

($M_aO_{b-d}$) represents the composition of the metal-oxygen cluster portion of the substituted polyoxometalate, the substituted polyoxometalate comprising one or more metals, M, which may be the same or different, selected from molybdenum, tungsten, vanadium, niobium, tantalum or a combination thereof; and, O is oxygen;

N is nitrogen;

$R^1$ is a substituent selected from substituted or unsubstituted hydrocarbyl or substituted or unsubstituted heterohydrocarbyl;

$R^2$ is a substituent selected from hydrogen, substituted or unsubstituted hydrocarbyl or substituted or unsubstituted heterohydrocarbyl;

a represents the number of metal atoms;

d represents the number of amine-derived substituents on the polyoxometalate;

b–d represents the number of oxygen atoms, the number of oxygen atoms decreasing as the number of amine-derived substituents increases; and, q represents the net charge of the substituted polyoxometalate.

102. The process of claim 101 wherein a ranges from about 6 to about 18.

103. The process of claim 102 wherein d ranges from about 1 to about 18.

104. The process of claim 103 wherein b ranges from about 19 to about 62.

105. The process of claim 90 wherein the substituted polyoxometalate has an average composition represented by the structure:

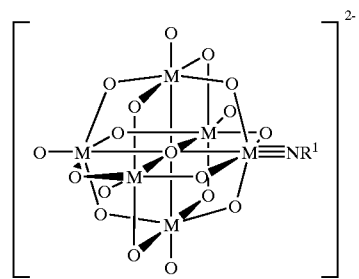

wherein M is a metal selected from the group consisting of molybdenum, tungsten, vanadium, niobium, tantalum, or a combination thereof, provided at least one of the metal atoms is molybdenum, N is nitrogen, O is oxygen and $R^1$ a substituent selected from the group consisting of substituted or unsubstituted hydrocarbyl.

* * * * *